US005646030A

United States Patent [19]

Ray et al.

[11] Patent Number: 5,646,030
[45] Date of Patent: Jul. 8, 1997

[54] METHOD FOR ISOLATING MUTANT CELLS

[75] Inventors: Bryan L. Ray, Burlington; Edmund C. C. Lin, Boston, both of Mass.; Roberto Crea, San Mateo, Calif.

[73] Assignee: President and Fellows of Harvard College, Cambridge, Mass.

[21] Appl. No.: 294,386

[22] Filed: Aug. 23, 1994

Related U.S. Application Data

[63] Continuation-in-part of Ser. No. 991,115, Dec. 16, 1992, Pat. No. 5,348,872, which is a continuation-in-part of Ser. No. 856,876, Mar. 24, 1992, abandoned, which is a continuation of Ser. No. 541,895, Jun. 21, 1990, abandoned.

[51] Int. Cl.$^6$ ................... C12N 5/00; C12P 21/06
[52] U.S. Cl. ................ 435/172.3; 435/5; 435/69.1; 435/172.1; 435/235.1; 435/239; 435/252.3; 435/252.33; 435/254.11; 435/373
[58] Field of Search ................ 435/172.1, 172.3, 435/69.1, 240.2, 252.3, 252.33, 320.1, 254.11, 235.1, 239, 240.1, 5

[56] References Cited

U.S. PATENT DOCUMENTS

| | | | |
|---|---|---|---|
| 4,421,849 | 12/1983 | Breuker | 435/32 |
| 5,223,409 | 6/1993 | Ladner et al. | 435/69.7 |
| 5,403,484 | 4/1995 | Ladner et al. | 435/235.1 |

FOREIGN PATENT DOCUMENTS

| | | |
|---|---|---|
| WO88/06630 | 9/1988 | WIPO. |
| WO90/04041 | 4/1990 | WIPO. |
| WO91/19799 | 12/1991 | WIPO. |

OTHER PUBLICATIONS

Becker et al. (1970) *Immunochem.* 7:741.
Hurwitz et al. (1970) *Eur. J. Biochem.* 17:273–277.
Pai (1972) *J. Bacteriol.* 112:1280.
Gurari et al. (1972) *Eur. J. Biochem.* 26:247.
Oger et al. (1974) *Proc. Natl. Acad. Sci.* (USA) 71:1554–1558.
Kempe et al. (1976) *Cell* 9:541.
Grull et al. (1979) *J. Bacteriol. 1* 137:480.
Yamada et al. (1982) *Agric. Biol. Chem.* 46:47.
Maniatis et al. *Molecular Cloning: A Laboratory Manual*, Cold Spring Harbor Laboratories, Cold Spring Harbor, NY (1982) pp. 78–79.
Vincenzotto et al. (1982) *Arch. Internat. de Chemi* 90:B88.
Yamada et al. (1983) *Agric. Biol. Chem.* 47:1011.
Frischauf et al. (1983) *J. Mol. Biol.* 170:827–842.
Santhaguru et al. (1985) *Israel J. Med. Sci.* 21:185.
Hibberd (1988) *Iowa State J. Res.* 62:479.
Hall et al. (1989) *J. Bacteriol.* 143:981.
LiMuti et al. (1989) *Microbiol. Meth.* 9:129.
Green (2d Chem. Congress N. Am. Continent, San Francisco, Aug. 22, 1989, Abst. No. 16).
Scott et al. (1990) *Science* 249:386.
Devlin et al. (1990) *Science* 249:404.
Scharf "Cloning with PCR" in *PCR Protocols. A Guide to Methods and Applications* (Innis et al., eds.) Academic Press, San Diego, CA (1990) pp. 84–91.
Chattopadhyay et al. (1991) *J. Gen. Microbiol.* 137:685.
Garrard et al. (1991) *Bio/Technol.* 9:1373.
Barbas et al. (1991) *Proc. Natl. Acad. Sci.* (USA) 88:7978.
Kornberg et al. (1991) *DNA Replication* (2d ed.) W.H. Freeman, New York, p. 172.
Schmidt et al. (1993) *Protein Engin.* 6:109–122.
Hohn (1979) *Meth. Enzymol.* 68:299–309.
Katsura (1976) *Molec. Gen. Genet.* 148:31.

*Primary Examiner*—Stephen G. Walsh
*Assistant Examiner*—Kenneth A. Sorensen
*Attorney, Agent, or Firm*—Lappin & Kusmer LLP

[57] ABSTRACT

Disclosed is a method for isolating a mutant cell that excretes a desired compound. The method includes culturing a plurality of auxotrophic pretreated starter cells and auxotrophic feeder cells in the presence of a reversibly noninfective, modified lambdoid bacteriophage. If the treated starter cell produces the desired compound, the bacteriophage will be rendered infective and infect the feeder cell. The feeder cell, in turn, will excrete a metabolite required by the starter cell and the starter cell will excrete a metabolite required by the feeder cell, enabling the cells to cross-feed, grow, and produce a colony containing a starter cell which produces the desired compound.

22 Claims, 12 Drawing Sheets

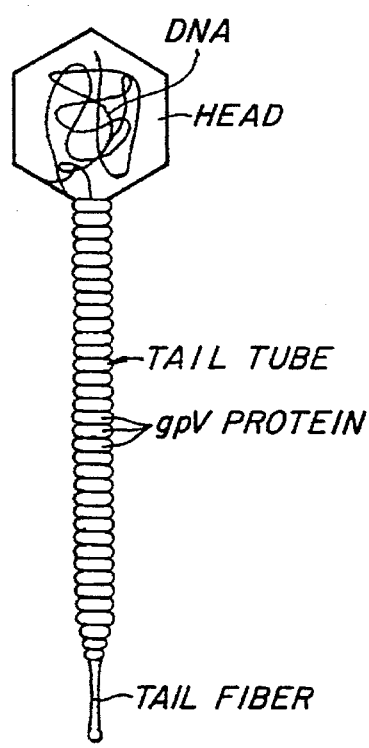 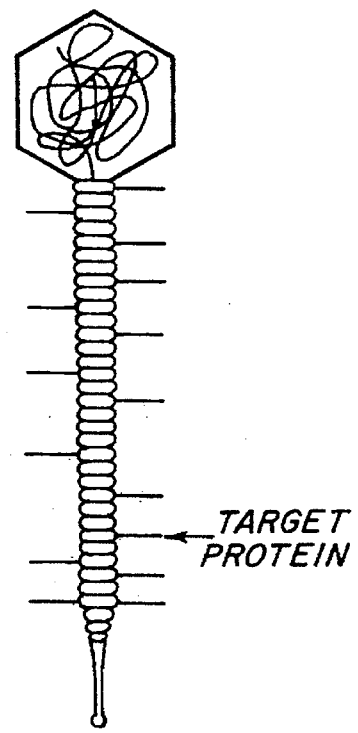
*FIG. 1A*  *FIG. 1B*

```
       M  F  V  F  N  F  T  M  P  V  K
      ATGCCTGTACCAAATCCTACAATGCCGGTGAA

G  A  G  T  T  L  W  V  Y  K  G  S  G  D  P  Y
 AGGTGCCGGCACCACCCTGTGGGTTTATAAGGGGAGCGGTGACCCTTACG

A  N  P  L  S  D  V  D  W  S  R  L  A  K  V  K  D
 CGAATCCGCTTTCAGACGTTGACTCGTCGCGTCTGGCAAAAGTTAAAGAC

L  T  P  G  E  L  T  A  E  S  Y  D  D  S  Y  L  D
    CTGACGCCCGGCGAACTGACCGCTGAGTCCTATGACGACAGCTATCTCGA

D  E  D  A  D  W  T  A  T  G  Q  G  Q  K  S  A
     TGATGAAGATGCAGACTGGACTGCGACCGGGCAGGGGCAGAAATCTGCCG

G  D  T  S  F  T  L  A  W  M  P  G  E  Q  G  Q  Q
 GAGATACCAGCTTCACGCTGGCGTGGATGCCCGGAGAGCAGGGGCAGCAG

A  L  L  A  W  F  N  E  G  D  T  R  A  Y  K  I  R
  GCGCTGCTGGCGTGGTTTAATGAAGGCGATACCCGTGCCTATAAAATCCG

F  P  N  G  T  V  D  V  F  R  G  W  V  S  S  I
      CTTCCCGAACGGCACGGCACATGTGTTCCGTGGCTGGGTCAGCAGTATCG

G  K  A  V  T  A  K  E  V  I  T  R  T  V  K  V  T
  GTAAGGCGGTGACGGCGAAGGAAGTGATCACCCGCACGGTGAAAGTCACC

N  V  G  R  P  S  M  A  E  D  R  S  T  V  T  A  A
   AATGTGGGACGTCCGTCGATGGCAGAAGATCGCAGCACGGTAACAGCGGC

T  G  M  T  V  T  P  A  S  T  S  V  V  K  G  Q
     AACCGGCATGACCGTGACGCCTGCCAGCACCTCGGTGGTGAAAGGGCAGA

S  T  T  L  T  V  A  F  Q  P  E  G  V  T  D  K  S
  GCACCACGCTGACCGTGGCCTTCCAGCCGGAGGGCGTAACCGACAAGAGC

F  R  A  V  S  A  D  K  T  K  A  T  V  S  V  S  G
  TTTCGTGCGGTGTCTGCGGATAAAACAAAAGCCACCGTGTCGGTCAGTGG

M  T  I  T  V  N  G  V  A  A  G  K  V  N  I  P
    TATGACCATCACCGTGAACGGCGTTGCTGCAGGCAAGGTCAACATTCCGG

V  V  S  G  N  G  E  F  A  A  V  A  E  I  T  V  T
  TTGTATCCGGTAATGGTGAGTTTGCTGCGGTTGCAGAAATTACCGTCACC

A  S
  GCCAGT
```

FIG. 2

```
                               M  P  V  P  N  P  T  M  P  V  K
                              ATGCCTGTACCAAATCCTACAATGCCGGTGAA

G   A  G  T  T  L  W  V  Y  K  G  S  G  D  P  Y
         AGGTGCCGGGACCACCCTGTGGGTTTATAAGGGGAGCGGTGACCCTTACG

A  N  P  L  S  D  V  D  W  S  R  L  A  K  V  K  D
         CGAATCCGCTTTCAGACGTTGACTGGTCGCGTCTGGCAAAAGTTAAAGAC

L  T  P  G  E  L  T  A  E  S  Y  D  D  S  Y  L  D
            CTGACGCCCGGCGAACTGACCGCTGAGTCCTATGACGACAGCTATCTCGA

D  E  D  A  D  W  T  A  T  G  Q  G  Q  K  S  A
            TGATGAAGATGCAGACTGGACTGCGACCGGGCAGGGGCAGAAATCTGCCG

G  D  T  S  F  T  L  A  W  M  P  G  E  Q  G  Q  Q
          GAGATACCAGCTTCACGCTGGCGTGGATGCCCGGAGAGCAGGGGCAGCAG

A  L  L  A  W  F  N  E  G  D  T  R  A  Y  K  I  R
          GCGCTGCTGGCGTGGTTTAATGAAGGCGATACCCGTGCCTATAAAATCCG

F  P  N  G  T  V  D  V  F  R  G  W  V  S  S  I
           CTTCCCGAACGGCACGGTCGATGTGTTCCGTGGCTGGGTCAGCAGTATCG

G  K  A  V  T  A  K  E  V  I  T  R  T  V  K  V  T
          GTAAGGCGGTGACGGCGAAGGAAGTGATCACCCGCACGGTGAAAGTCACC

N  V  G  R  P  S  M  A  E  D  R  S  T  V  T  A  A
           AATGTGGGACGTCCGTCGATGGCAGAAGATCGCAGCACGGTAACAGCGGC

T  G  M  T  V  T  P  A  S  T  S  V  V  K  G  Q
            AACCGGCATGACCGTGACGCCTGCCAGCACCTCGGTGGTGAAAGGGCAGA

S  T  T  L  T  V  A  F  Q  P  E  G  V  T  D  K  S
           GCACCACGCTGACCGTGGCCTTCCAGCCGGAGGGCGTAACCGACAAGAGC

F  R  A  V  S  A  D  K  T  K  A  T  V  S  V  S  G
            TTTCGTGCGGTGTCTGCGGATAAAACAAAAGCCACCGTGTCGGTCAGTGG

M  T  I  T  V  N  G  V  A  A  G  K  V  N  I  P
            TATGACCATCACCGTGAACGGCGTTGCTGCAGGCAAGGTCAACATTCCGG

V  V  S  G  N  G  E  F  A  A  V  A  E  I  T  V  T
           TTGTATCCGGTAATGGTGAGTTTGCTGCGGTTGCAGAAATTACCGTCACC

A  C
           GCCTGT
```

FIG. 3

CONSTRUCTION OF STREP-TAG ENCODING DNA SEGMENT

Oligo A: 5'- CCGCTTGGCGTCACCCGCAGTTCGGTGGTTA -3'

Oligo B: 5'- AGCTTAACCACCGAACTGCGGGTGACGCCAAGCGG -3'

↓ ANNEAL

5'- CCGCTTGGCGTCACCCGCAGTTCGGTGGTTA    -3'
3'- GGCGAACCGCAGTGGGCGTCAAGCCACCAATTCGA -5'

*FIG. 11*

CONSTRUCTION OF pSYM27 pSYM1: REGION SURROUNDING C-TERMINUS OF V GENE.

```
                        Cys246
............GTCACCGCCTGTTAACTGCAGGAAGCTTCGGG........
............CAGTGGCGGACAATTGACGTCCTTCGAAGCCC........
                    HpaI          HindIII
```

DIGEST w/
HpaI & HindIII

↓

```
     Cys246
GTCACCGCCTGTT                                    AGCTTCGGG
CAGTGGCGGACAA                                         AGCCC
```

+

STREP-TAG
```
CCGCTTGGCGTCACCCGCAGTTCGGTGGTTA
GGCGAACCGCAGTGGGCGTCAAGCCACCAATTCGA
```

LIGATE

↓

```
        Cys246
...GTCACCGCCTGTTCGGCTTGGCGTCACCCGCAGTTCGGTGGTTAAGCTTCGGG...
...CAGTGGCGGACAAGGCGAACCGCAGTGGGCGTCAAGCCACCAATTCGAAGCCC...
    Strep-tag:   SerAlaTrpArgHisProGlnPheGlyGlyEnd
```

*FIG. 12*

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 246 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:1:

```
Met Pro Val Pro Asn Pro Thr Met Pro Val Lys Gly Ala Gly Thr Thr
 1               5                  10                 15
Leu Trp Val Tyr Lys Gly Ser Gly Asp Pro Tyr Ala Asn Pro Leu Ser
            20                  25                 30
Asp Val Asp Trp Ser Arg Leu Ala Lys Val Lys Asp Leu Thr Pro Gly
        35                  40                 45
Glu Leu Thr Ala Glu Ser Tyr Asp Asp Ser Tyr Leu Asp Asp Glu Asp
    50                  55                 60
Ala Asp Trp Thr Ala Thr Gly Gln Gly Gln Lys Ser Ala Gly Asp Thr
65                  70                  75                 80
Ser Phe Thr Leu Ala Trp Met Pro Gly Glu Gln Gly Gln Gln Ala Leu
                85                  90                 95
Leu Ala Trp Phe Asn Glu Gly Asp Thr Arg Ala Tyr Lys Ile Arg Phe
            100                 105                110
Pro Asn Gly Thr Val Asp Val Phe Arg Gly Trp Val Ser Ser Ile Gly
        115                 120                125
Lys Ala Val Thr Ala Lys Glu Val Ile Thr Arg Thr Val Lys Val Thr
    130                 135                140
Asn Val Gly Arg Pro Ser Met Ala Glu Asp Arg Ser Thr Val Thr Ala
145                 150                 155                160
Ala Thr Gly Met Thr Val Thr Pro Ala Ser Thr Ser Val Val Lys Gly
                165                 170                175
Gln Ser Thr Thr Leu Thr Val Ala Phe Gln Pro Glu Gly Val Thr Asp
            180                 185                190
Lys Ser Phe Arg Ala Val Ser Ala Asp Lys Thr Lys Ala Thr Val Ser
        195                 200                205
Val Ser Gly Met Thr Ile Thr Val Asn Gly Val Ala Ala Gly Lys Val
    210                 215                220
Asn Ile Pro Val Val Ser Gly Asn Gly Glu Phe Ala Ala Val Ala Glu
225                 230                 235                240
```

Ile Thr Val Thr Ala Ser
              245

( 2 ) INFORMATION FOR SEQ ID NO:2:

( i ) SEQUENCE CHARACTERISTICS:
      ( A ) LENGTH: 741 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

| | | | | | |
|---|---|---|---|---|---|
| ATGCCTGTAC | CAAATCCTAC | AATGCCGGTG | AAAGGTGCCG | GGACCACCCT | GTGGGTTTAT | 60 |
| AAGGGGAGCG | GTGACCCTTA | CGCGAATCCG | CTTTCAGACG | TTGACTGGTC | GCGTCTGGCA | 120 |
| AAAGTTAAAG | ACCTGACGCC | CGGCGAACTG | ACCGCTGAGT | CCTATGACGA | CAGCTATCTC | 180 |
| GATGATGAAG | ATGCAGACTG | GACTGCGACC | GGGCAGGGGC | AGAAATCTGC | CGGAGATACC | 240 |
| AGCTTCACGC | TGGCGTGGAT | GCCCGGAGAG | CAGGGGCAGC | AGGCGCTGCT | GGCGTGGTTT | 300 |
| AATGAAGGCG | ATACCGTGC | CTATAAAATC | CGCTTCCCGA | ACGGCACGGT | CGATGTGTTC | 360 |
| CGTGGCTGGG | TCAGCAGTAT | CGGTAAGGCG | GTGACGGCGA | AGGAAGTGAT | CACCCGCACG | 420 |
| GTGAAAGTCA | CCAATGTGGG | ACGTCCGTCG | ATGGCAGAAG | ATCGCAGCAC | GGTAACAGCG | 480 |
| GCAACCGGCA | TGACCGTGAC | GCCTGCCAGC | ACCTCGGTGG | TGAAAGGGCA | GAGCACCACG | 540 |
| CTGACCGTGG | CCTTCCAGCC | GGAGGGCGTA | ACCGACAAGA | GCTTTCGTGC | GGTGTCTGCG | 600 |
| GATAAAACAA | AAGCCACCGT | GTCGGTCAGT | GGTATGACCA | TCACCGTGAA | CGGCGTTGCT | 660 |
| GCAGGCAAGG | TCAACATTCC | GGTTGTATCC | GGTAATGGTG | AGTTTGCTGC | GGTTGCAGAA | 720 |
| ATTACCGTCA | CCGCCAGTTA | A | | | | 741 |

( 2 ) INFORMATION FOR SEQ ID NO:3:

( i ) SEQUENCE CHARACTERISTICS:
      ( A ) LENGTH: 246 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:3:

Met Pro Val Pro Asn Pro Thr Met Pro Val Lys Gly Ala Gly Thr Thr
 1               5                  10                 15

Leu Trp Val Tyr Lys Gly Ser Gly Asp Pro Tyr Ala Asn Pro Leu Ser
             20                 25                 30

Asp Val Asp Trp Ser Arg Leu Ala Lys Val Lys Asp Leu Thr Pro Gly
         35                 40                 45

Glu Leu Thr Ala Glu Ser Tyr Asp Asp Ser Tyr Leu Asp Asp Glu Asp
     50                 55                 60

Ala Asp Trp Thr Ala Thr Gly Gln Gly Gln Lys Ser Ala Gly Asp Thr
65                 70                 75                 80

Ser Phe Thr Leu Ala Trp Met Pro Gly Glu Gln Gly Gln Gln Ala Leu

|   |   |   |   |   | 85 |   |   |   |   | 90 |   |   |   |   | 95 |   |   |
|---|---|---|---|---|---|---|---|---|---|---|---|---|---|---|---|---|---|
| Leu | Ala | Trp | Phe 100 | Asn | Glu | Gly | Asp | Thr 105 | Arg | Ala | Tyr | Lys | Ile 110 | Arg | Phe |
| Pro | Asn | Gly 115 | Thr | Val | Asp | Val | Phe 120 | Arg | Gly | Trp | Val | Ser 125 | Ser | Ile | Gly |
| Lys | Ala 130 | Val | Thr | Ala | Lys | Glu 135 | Val | Ile | Thr | Arg | Thr 140 | Val | Lys | Val | Thr |
| Asn 145 | Val | Gly | Arg | Pro | Ser 150 | Met | Ala | Glu | Asp | Arg 155 | Ser | Thr | Val | Thr | Ala 160 |
| Ala | Thr | Gly | Met | Thr 165 | Val | Thr | Pro | Ala | Ser 170 | Thr | Ser | Val | Val | Lys 175 | Gly |
| Gln | Ser | Thr | Thr 180 | Leu | Thr | Val | Ala | Phe 185 | Gln | Pro | Glu | Gly | Val 190 | Thr | Asp |
| Lys | Ser | Phe 195 | Arg | Ala | Val | Ser | Ala 200 | Asp | Lys | Thr | Lys | Ala 205 | Thr | Val | Ser |
| Val | Ser 210 | Gly | Met | Thr | Ile | Thr 215 | Val | Asn | Gly | Val | Ala 220 | Ala | Gly | Lys | Val |
| Asn 225 | Ile | Pro | Val | Val | Ser 230 | Gly | Asn | Gly | Glu | Phe 235 | Ala | Ala | Val | Ala | Glu 240 |
| Ile | Thr | Val | Thr | Ala 245 | Cys |   |   |   |   |   |   |   |   |   |   |

( 2 ) INFORMATION FOR SEQ ID NO:4:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( i x ) FEATURE:
        ( A ) NAME/KEY: misc. feature
        ( B ) LOCATION:
        ( D ) OTHER INFORMATION: standardname ="5'Primer"

( x i ) SEQUENCE DESCRIPTION: SEQ ID NO:4:

CGGGAATTCA ATGCCTGTAC CAAATCCTAC AATG        34

( 2 ) INFORMATION FOR SEQ ID NO:5:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( i x ) FEATURE:
        ( A ) NAME/KEY: misc. feature
        ( B ) LOCATION:
        ( D ) OTHER INFORMATION: standardname ="3'Primer"

( x i ) SEQUENCE DESCRIPTION: SEQ ID NO:5:

CCCGAAGCTT CCTGCAGTTA ACAGGCGGTG ACGGTAATTT CTGCAAC        47

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:6:

GTTGCTGCAG GTATGGCTTT CATGGAGCAT TCA        33

( 2 ) INFORMATION FOR SEQ ID NO:7:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:7:

CCGCTGCAGC TACATTTCCT TGTCGTTAG        29

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( x i ) SEQUENCE DESCRIPTION: SEQ ID NO:8:

Ser  Phe  Cys  Phe  Gly  Gly
    1                     5

( 2 ) INFORMATION FOR SEQ ID NO:9:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( i x ) FEATURE:
        ( A ) NAME/KEY: misc. feature
        ( B ) LOCATION:
        ( D ) OTHER INFORMATION: standardname ="5'Primer"

( x i ) SEQUENCE DESCRIPTION: SEQ ID NO:9:

CCGCTGCAGG AATGACCATG ATTACGGATT C   31

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (ix) FEATURE:
        (A) NAME/KEY: misc. feature
        (B) LOCATION:
        (D) OTHER INFORMATION: standardname ="3'Primer"

(xi) SEQUENCE DESCRIPTION: SEQ ID NO:10:

CCGAAGCTTA ACGACTGTCC TGGCCGTAAC   30

(2) INFORMATION FOR SEQ ID NO:11:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:11:

Ser Ala Trp Arg His Pro Gln Phe Gly Gly
1               5                   10

(2) INFORMATION FOR SEQ ID NO:12:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (ix) FEATURE:
        (A) NAME/KEY: misc. feature
        (B) LOCATION:
        (D) OTHER INFORMATION: standardname ="5'Primer"

(xi) SEQUENCE DESCRIPTION: SEQ ID NO:12:

CCGCTTGGCG TCACCCGCAG TTCGGTGGTT A   31

(2) INFORMATION FOR SEQ ID NO:13:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (ix) FEATURE:
  (A) NAME/KEY: misc. feature
  (B) LOCATION:
  (D) OTHER INFORMATION: standardname ="3'Primer"

(xi) SEQUENCE DESCRIPTION: SEQ ID NO:13:

AGCTTAACCA CCGAACTGCG GGTGACGCCA AGCGG    35

(2) INFORMATION FOR SEQ ID NO:14:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: no (xi) SEQUENCE DESCRIPTION: SEQ ID NO:14:

GTCACCGCCT GTTAACTGCA GGAAGCTTCG GG    32

(2) INFORMATION FOR SEQ ID NO:15:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: yes (xi) SEQUENCE DESCRIPTION: SEQ ID NO:15:

CAGTGGCGGA CAATTGACGT CCTTCGAAGC CC    32

(2) INFORMATION FOR SEQ ID NO:16:

(i) SEQUENCE CHARACTERISTICS:
    (A) LENGTH: 13 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: no (xi) SEQUENCE DESCRIPTION: SEQ ID NO:16:

GTCACCGCCT GTT    13

(2) INFORMATION FOR SEQ ID NO:17:

(i) SEQUENCE CHARACTERISTICS:
    (A) LENGTH: 13 base pairs
    (B) TYPE: nucleic acid
    (C) STRANDEDNESS: single
    (D) TOPOLOGY: linear (ii) MOLECULE TYPE: DNA (iii) HYPOTHETICAL: NO -continued (iv) ANTI-SENSE: yes (xi) SEQUENCE DESCRIPTION: SEQ ID NO:17:

CAGTGGCGGA CAA  13

(2) INFORMATION FOR SEQ ID NO:18:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: no (xi) SEQUENCE DESCRIPTION: SEQ ID NO:18:

AGCTTCGGG  9

(2) INFORMATION FOR SEQ ID NO:19:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: yes (xi) SEQUENCE DESCRIPTION: SEQ ID NO:19:

AGCCC  5

(2) INFORMATION FOR SEQ ID NO:20:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: no (xi) SEQUENCE DESCRIPTION: SEQ ID NO:20:

GTCACCGCCT GTTCCGCTTG GCGTCACCCG CAGTTCGGTG GTTAAGCTTC GGG  53

METHOD FOR ISOLATING MUTANT CELLS

CROSS-REFERENCE TO RELATED APPLICATIONS

The subject matter of this application is a continuation-in-part of (allowed) application Ser. No. 07/991,115, entitled "Method of Isolating Mutant Cells," filed Dec. 16, 1992, now U.S. Pat. Ser. No. 5,348,572, which is a continuation-in-part of application Ser. No. 07/556,876, entitled "Method of Isolating Mutant Cells," filed Mar. 24, 1992, now abandoned, which was a file-wrapper-continuation of Ser. No. 07/541,895, filed Jun. 21, 1990, now abandoned.

BACKGROUND OF THE INVENTION

This invention relates to screening methods for cells and for molecules of interest. More particularly, this invention relates to methods of isolating a mutant cell which expresses a desired compound utilizing lambdoid bacteriophage infection and the formation of a symbiotic relationship between two different cell types.

It is common to isolate mutant cells which overproduce a specific metabolite by selecting cells which are resistant to analogs of the metabolite. For example, Yamada et al. (*Agric. Biol. Chem.* (1983) 47:1011) describe the isolation of mutants which overproduce biotin by selecting for cells resistant to a biotin analog. Yamada et al. (*Agric. Biol. Chem.* (1982) 46:47) and Chattopadhyay et al. (*J. Gen. Microbiol* (1991) 137:685) isolated methionine overproducing mutants by selecting cells resistant to ethionine. Hifferd (*Iowa State J. Res.* (1988) 62: 479) isolated valine-overproducing mutants, selecting for valine resistance. Kempe et al. (*Cell* (1976) 9:541) isolated pyrimidine nucleotide biosynthetic enzyme overproducers, selecting for resistance to N-phosphonoacetyl-l-aspartate. Hall et al. (*J. Bactriol.* (1989) 143:981), isolated amino acid overproducers in cyanobacteria by selecting for antimetabolite analog resistance. In Hall et al. (ibid. ) wild type *Bacillus subtilis* cells were used as a test lawn for screening obvious regulatory mutants from among collections of analog resistant strains. Auxotrophic strains of *B. subtillis* were convenient indicator strains for identification of mutants in *Cyanobacteria* through observation of syntrophic growth responses. Green (2d Chem. Congress N. Am. Continent, San Francisco, Aug. 22, 1989, Abst. No. 16) describes production of mutant corn cells resistant to lysine- and threonine-induced growth inhibition. Grull et al. (*J. Bacteriol.* 1 (1979) 137:480) describe isolation of amino acid overproducing mutants of *Escherichia coli* (*E. coli*) obtained by mutagenesis and penicillin enrichment. Vincenzotto et al. (*Arch. Internat. de Chemi* (1982) 90:B88) describe isolation of mutants of an alga by mutagenesis and screening on agar medium containing various dyes. Santhaguru et al.(*Israel J. Med. Sci.* (1985) 21:185) describe use of levulinate, a competitive inhibitor of the heme biosynthetic pathway, for isolation of heme overproducing *Rhizobium* mutants.

Isolation of cells that produce a desired compound from a population of cells that do not make the desired compound is a problem when the production of the desired compound does not endow the cell with any selective advantage. In these instances, a method of screening rather than selecting for production of the desired product must be developed. A screening method which employs a detector strain present in an overlay was utilized by Pai (*J. Bacteriol.* (1972) 112:1280) to isolate a strain that overproduces biotin. In this method, wild type *E. coli* were mutagenized and plated with an *E. coli* biotin auxotroph. The mutagenized *E. coli* was not itself an auxotroph, and thus, a mutual two-way symbiotic relationship was not achieved. A similar method has more recently been employed to screen for lysine excretors (LiMuti et al. (1989) *Microbiol Meth.* 9:129). A variation of the overlay method has been developed where a micropore membrane is used to separate the strain from the substrate (U.S. Pat. No. 4,421,849). A problem with these strategies is the limitation on the number of cells that can be screened at one time. The limit is based on the need to distinguish individual colonies on a plate which places the limit, e.g. for bacteria, at 1000 to 10,000 per each 100 mm diameter plate. If the event resulting in production of the desired compound occurs at a frequency of $10^{-7}$, then 1000 plates would have to be screened to obtain one event.

Bacteriophages have been used in strategies for detecting desired compounds. For example, a method employing the bacteriophage M13 has been used to assay for various proteins of interest. In this method, M13 bacteriophage displaying peptides fused to pIII, a minor M13 coat protein, have been used to screen for protein binding molecules and antibodies (Scott et al. (1990) *Science* 249:386; Devlin et al. (1990) *Science* 249:404). Special M13-derived systems have been used to express antibodies as fusion proteins on the surface of the bacteriophage, and techniques have been developed to enrich the population for bacteriophage expressing antibodies with desired affinities for an antigen (Garrard et al. (1991) *Bio/Technol.* 9:1373; Barbas et al. (1991) *Proc. Natl. Acad. Sci.* (USA) 88:7978). However, the use of M13 in assay methods is limited because M13 infection is not immediately ascertainable. This is because infection by M13 does not provide the cell with compounds required for growth and is not lytic.

Like M13, T4 has been used in assays for various proteins such as nerve growth factor (NGF) (Oger et al. (1974) *Proc. Natl. Acad. Sci.* (USA) 71:1554–1558). In this assay, T4 was chemically coupled to NGF using glutaraldehyde. The bacteriophage was then rendered non-infective by treatment with antibodies against NGF. When unbound NGF was added to the medium, NGF-linked bacteriophage was displaced from the antibody and became free to infect *E. coli*. Bacteriophage T4 has also been used to detect antibodies against a wide range of compounds. For example, Becker et al. (*Immunochem.* (1970) 7:741) used a T4 bacteriophage to detect antibodies against p-azobenzenearsonate. Hurwitz et al. (*Eur. J. Biochem.* (1970) 17:273) used a T4 bacteriophage to detect and estimate levels of angiotensin-II-beta-amide and its antibodies. Gurari et al. (*Eur. J. Biochem.* (1972) 26:247) used bacteriophage T4 in the detection of antibodies to nucleic acids. These detection methods involve the chemical modification of the T4 bacteriophage resulting in the non-specific exposure on the bacteriophage surface of a compound to which the antibodies to be assayed are targeted. Such antibodies render the bacteriophage non-infective, thus enabling the decrease in plaque formation to be used as a measure of the level of antibody present. The T4 system has also been used to measure hapten concentrations (see, e.g., Hurwitz et al. (1970) *Eur. J. Biochem.* 17:273–277) In this system, T4 is chemically modified such that it exposes the desired hapten non-specifically on its surface. The addition of anti-hapten antibody blocks the infectivity of the bacteriophage. Infectivity is restored in the presence of hapten.

Although both the M13 and T4 bacteriophage systems can be used to detect the presence of a desired compound (or a cell producing that compound) by their ability to become infectious in the presence of that compound (and thus in the presence of a cell producing that compound), infection by M13 is normally not immediately ascertainable, and T4 infection is lethal. Thus, these systems cannot be used where a quick selection method based on the survival of the infected bacterial cell is desired, such as where a particular cell type is being selected, or when the object of bacteriophage infection is to restore the ability of an auxotrophic bacterial cell to survive on its own under a given set of growth conditions. Special M13-derived phagemid systems carry genes which could endow an infected cell with a selective growth advantage (Barbas et al. (1991) *Proc. Natl. Acad. Sci.* (USA) 88:7978). However, these systems have not been used to detect a desired compound or cells producing such compounds. Furthermore, because gpIII, the M13 protein to which the target molecules are fused, accumulates on the inner membrane facing the periplasm, there are limitations on the nature of the protein fusion. Fusions that are not able to cross the membrane will not be assembled into M13. In addition, in all M13 systems where fusion proteins have been used to display proteins on the outer surface, the displayed protein (or peptide) itself has been the desired compound.

Thus, what is needed are new methods for selecting cells that excrete desired compounds. What is also needed are selection methods that do not limit the desired compounds to those on which cell growth is dependent. In addition, what is needed are selection methods that do not limit the desired compounds to those that can be assayed based on changes in color, turbidity or viscosity. Finally, what are needed are selection methods that are adaptable to a broad range of cell types.

SUMMARY OF THE INVENTION

It has been discovered that lambdoid bacteriophage having a target molecule peptide linked to one of its components, the gpV protein, can be successfully assembled in vivo such that the target molecule is displayed on the outer surface of the bacteriophage. It has also been discovered that such a modified lambdoid bacteriophage maintains its ability to infect *E. coli*. These findings have been exploited to develop the present invention, namely, methods of selecting a cell producing a desired compound utilizing such modified lambdoid bacteriophage.

The method further involves the symbiotic amplification of a selected mutant cell which produces a desired compound by using two genetically different populations of auxotrophic cells which cross-feed each other.

The term "mutant cell" is meant to encompass any cell whose total cellular genetic composition has been altered, for example, by chemical mutagenesis, spontaneous mutation, genetic engineering, transformation, or transfection, such that its ability to produce the desired compound is affected.

In this method a starter cell is provided which is a protist, monera, fungi, plant, animal, or human cell. As used herein, the term "protist" refers to a single-celled protozoa, eukaryotic algae and slime molds. The term "monera" refers to a single-celled organism which comprises bacteria and blue-green algae. This starter cell is an auxotroph that has a requirement for a first metabolite for its growth in a solid growth medium, and mutates to lack this requirement at a frequency of less than $10^{-10}$ per cell division. In addition, the starter cell is resistant to lambdoid bacteriophage infection, which, in some embodiments, is the result of a mutation within the cell, such as one in the bacteriophage receptor. The starter cell excretes a second metabolite into the medium, and is able to grow on media that supports the growth of bacteria.

As used herein, "excretes" encompasses active transport, passive transport or unfacilitated diffusion from the cell.

The first metabolite produced by the feeder cell includes any compound which will enable or aid in the survival and growth of the starter cell, and in which the starter cell is deficient. The second metabolite produced by the starter cell includes any compound which will aid in the growth of the feeder cell, and in which the feeder cell is deficient. However, the first and second metabolites are not the same and are not the same as the desired compound. In preferred embodiments, the first metabolite is a sugar, growth factor, enzyme, vitamin, amino acid, cytokine, lymphokine, interleukin, trophic factor, nucleic acid component, cofactor, fatty acid, lipid, glycolipid, glycoprotein, polysaccharide, lipopolysaccharide, lipoprotein, proteolipid, or proteoglycan and the second metabolite is a vitamin, amino acid, nucleic acid component, cofactor, sugar, or any molecule required for bacterial growth and maintenance. In another embodiment, the first or second metabolite is also a signalling compound which activates a metabolite in the growth medium which is required by the starter or feeder cells, or which stimulates the production of the metabolite by another source such as a third cell type.

In the method of the invention, the starter cell is treated so as to increase the probability that it will excrete the desired compound. In most preferred embodiments of the invention, the desired compound produced and excreted by the treated starter cell is a polypeptide, peptide, hormone, nucleic acid, carbohydrate, lipid, glycoprotein, glycolipid, proteolipid, lipoprotein, lipopolysaccharide, vitamin, toxin, terpene, antibiotic, or cofactor. In some preferred embodiments the desired compound includes a enzyme enzyme substrate, immunoglobulin, receptor, ligand, growth factor, toxin, cytokine, or hormone. In another embodiment, the desired compound is a factor which activates or stimulates the production of a compound by another cell which is not the feeder cell.

Treatment of the starter cell includes mutagenizing the starter cell with a chemical mutagen, in one instance. In another embodiment, treatment comprises genetically engineering the starter cell to express a mutator gene. Such forms of mutation result, in some embodiments, in a rate of mutation of at least $10^{-6}$ per mucleotide base per cell division. In other embodiments, the starter cell is treated by transfecting or transforming it with a vector containing a gene encoding, or involved in the production of, the desired compound. In some embodiments, the starter cell also has a selectable phenotype allowing for its isolation from the feeder cell.

The feeder cell is a bacterial cell that is susceptible to lambdoid bacteriophage infection. It excretes the first metabolite required by the starter cell into solid growth medium. In some embodiments, the feeder cell has a selectable phenotype allowing for its ready isolation from the starter cell. The feeder cell is also an auxotroph that requires the second metabolite and also a nutrient which is other than the first or second metabolite for its long term survival and proliferation in the solid growth medium. The feeder cell carries a mutation which increases the likelihood that bacteriophage infection will result in lysogenization. One such mutation is the hfla which stands for "high frequency of lysogenization".

As used herein, the term "nutrient" is meant to encompass a growth factor, enzyme, vitamin, amino acids, cytokine, interleukin, trophic factor, nucleic acid component, cofactor, fatty acid, lipid, glycolipid, glycoprotein, polysaccharide, lipopolysaccharide, lipoprotein or fatty acid whose production in the feeder cell is controlled directly or indirectly by the expression of a gene.

The starter and feeder cells may belong to the same or different taxonomical kingdoms, phyla, classes, orders, families, genera, or species. In one preferred embodiment of the invention, the feeder cell is an *Escherichia coli* (*E. coli*) and the starter cell is a protist, monera, fungi, animal, plant, or human cell. In some embodiments, the starter and/or the feeder cells have been genetically engineered or mutagenized to become auxotrophic.

In the next step of the method of the invention, a plurality of treated starter cells and feeder cells are cultured together on the solid growth medium in the presence of a reversibly noninfective, modified lambdoid bacteriophage. As used herein, the term "lambdoid bacteriophage" is meant to encompass all lambda-related bacteriophages and all derivatives, genetically engineered derivatives, and hybrids thereof, such as, but not limited to, φ80, φ81, bacteriophages 21, 82, 424, 432, λimm434, λimm21, phagemids, λEMBL, and λgt.

This lambdoid bacteriophage can be induced to produce a lytic infection. In some embodiments, this is the result of a mutation in the virus, such as one resulting in the temperature sensitive expression of the CI lambda repressor, which renders the virus temperature sensitive, thereby inducing lyric infection at certain temperatures which do not include the temperature at which the starter and feeder cells are cultured. Such a bacteriophage is called a temperate bacteriophage.

As used herein, the term "temperate bacteriophage" refers to a bacteriophage that can be lyric or lysogenic. When lysogenic, the bacteriophage integrates its nucleic acid into the host cell genome and remains quiescent, replicating only when the host genome replicates. In its lytic or vegetative multiplication state, the bacteriophage nucleic acid excises itself from the host genome, or does not integrate itself into the host cell genome, but rather takes over the protein synthetic machinery of the cell at the expense of cellular components and causes bacteriophage progeny to be assembled. New bacteriophage are released from the cell when the cell lyses. A temperate bacteriophage may contain a mutation conferring temperature sensitivity, i.e., it is lysogenic only at low growth temperatures (e.g., at or below about 32° C.) and is lytic at high growth temperatures (e.g., at about 37° C. and above, such as at about 42° C.). At higher temperatures, the phage is lytic. This is required to produce the phage for use in the screening system. At lower growth temperatures, the nonlytic, lysogenic bacteriophage DNA can integrate into the bacterial cell genome, providing the genome with a gene which the auxotrophic cell requires to survive. Preferably, such a gene encodes a polypeptide that provides the nutrient required by the feeder cell.

The lambdoid bacteriophage includes a modified gpV protein to which a target protein is linked. As used herein the term "gpV protein" is meant to encompass any major tail protein found in the lambdoid bacteriophages. This includes but is not limited to lambda gpV protein, gpV-related proteins and equivalents of lambda gpV protein in the tails of other lambdoid viruses.

In some embodiments, the bacteriophage contains a genetically modified gpV protein truncated at its carboxy terminus and peptide bonded at its carboxy terminus to the target molecule, which is a peptide containing molecule. Preferable peptide-containing target molecules include polypeptides, proteins, glycoproteins, proteoglycans, lipoproteins, or proteolipids. In some of these embodiments, the target molecule is an enzyme, enzyme substrate, receptor, immunoglobulin, or hormone.

In another embodiment the bacteriophage includes a chemically modified gpV protein having a chemically reactive amino acid residue in place of a native gpV amino acid residue and which is chemically linked to the target molecule. In one embodiment, this chemical linkage is a covalent linkage. Preferably, the chemically reactive amino acid residue is histidine (His), cysteine (Cys), tyrosine (Tyr), or tryptophan (Trp). Most preferably, the reactive amino acid residue is cysteine because it can be selectively modified. These reactive residues may be anywhere in the gpV amino acid sequence provided the modification does not interfere with gpV protein function or in bacteriophage assembly and structure. In one embodiment the reactive residue is at the carboxy terminus of the gpV protein. In another preferred embodiment, the modified gpV protein has a cysteine residue instead of a serine residue at its carboxy terminus. In some embodiments, the target molecule is chemically coupled to the chemically reactive amino acid residue either directly or via a chemical cross-linker such as a bifunctional cross-linking agent. As with the genetically modified gpV protein, the target molecule can be a peptide. In addition, as with the chemically modified gpV protein, preferable target molecules include proteins, peptides, carbohydrates, hormones, glycoproteins, proteoglycans, lipoproteins, proteolipids, lipids, lipopolysaccarides, toxins, cofactors, nucleic acids, glycolipids, terpenes, antibiotics, and vitamins.

The target molecule linked to the modified gpV protein of the bacteriophage is also bound by a binding molecule which renders the bacteriophage reversibly noninfective. In preferred embodiments, the binding molecule is an enzyme, enzyme substrate, immunoglobulin, receptor, ligand, or matrix, depending on what the target molecule is. For example, if the target molecule is an immunoglobulin or receptor, the binding molecule is another immunoglobulin which recognizes the immunoglobulin or receptor, or is a ligand or antigen to which the immunoglobulin or receptor binds.

As used herein, the term "ligand" refers to any molecule, the function of which is conveyed through binding to a specific protein. The term "matrix" refers to any solid support to which compounds can be attached including but not limited to Sephadex™, agarose, polystyrene and glass.

If at least one of the treated starter cells excretes the desired molecule, the noninfective bacteriophage will be released from the binding molecule, rendering it infective once again. In one embodiment, release is effectuated by the cleavage of the target molecule by the desired compound which is an enzyme. In another embodiment, the target molecule is released from the binding molecule when the desired compound, which is an unbound target molecule or a portion, analog, agonist, or antagonist thereof to which the binding molecule will bind, competes with the gpV-linked target molecule for the binding molecule. The infective bacteriophage then infects at least one of the feeder cells, bringing with it the gene for the polypeptide directly or indirectly responsible for the synthesis of the nutrient, enabling the infected feeder cell to produce the nutrient.

A colony is detected when the treated starter cell which excretes the desired compound excretes the first metabolite and the infected feeder cell excretes the second metabolite, thereby enabling the feeder and starter cells to grow and form a proliferative nucleus of cells. The treated starter cells are then isolated from the feeder cells in the colony.

By a "colony" is meant a group of cells including both starter and feeder cells which manifest themselves on the solid growth medium in a manner detectable by one of ordinary skill in the art. Generally, such colonies will be visible to a naked eye, having a size of greater than 0.1 mm.

Other features and advantages of this invention will be apparent from the following description of the preferred embodiments thereof, and from the claims.

BRIEF DESCRIPTION OF THE DRAWINGS

The foregoing and other objects of the present invention, the various features thereof, as well as the invention itself may be more fully understood from the following description, when read together with the accompanying drawings in which:

FIG. 1A is a diagrammatic representation of the bacteriophage lambda;

FIG. 1B is a diagrammatic representation of the modified lambdoid bacteriophage of the invention;

FIG. 2 is a schematic representation of the nucleic acid sequence and corresponding amino acid sequence of the gpV protein;

FIG. 3 is a schematic representation of the nucleic acid sequence and corresponding amino acid sequence of the gpV protein in which the C terminal $Ser_{246}$ has been replaced with Cys;

FIG. 11 is a diagrammatic representation of the construction of Strep-Tag encoding DNA segment;

FIG. 12 is a schematic representation of the development of plasmid pSYM27.

DESCRIPTION OF THE PREFERRED EMBODIMENT

Figure 4:
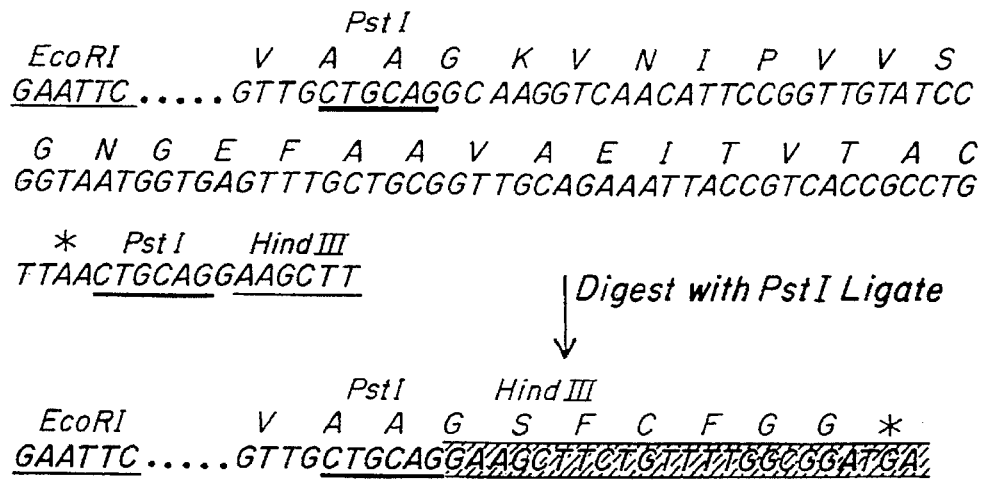
FIG. 4 is a schematic representation of the strategy for constructing the genetically modified truncated V gene with a multiple cloning site at its carboxy terminus.

A new method has been developed for the isolation of mutant cells which produce a desired compound. This method can be used to select for the excretion of desired compounds that are either produced naturally or are a product of genetic engineering, transfection, transformation, mutagenesis, or some other method. The procedure results in the isolation of a single mutant excreting cell from a population of non-excreting starter cells.

The basis of this method, and the feature that distinguishes it from all other selection methods currently employed, is the establishment of a symbiotic relationship between two auxotrophic cell types ultimately dependent on excretion of the desired compound. Mother feature of the method exploits the ability of a lambdoid bacteriophage modified in part by its linkage to a target protein, to retain its infectivity.

In this method two different auxotrophic cells, only one of which is susceptible to lambdoid bacteriophage infection, and each requiring for survival and growth a metabolite that the other excretes, are exposed to such a lambdoid bacteriophage which has been rendered reversibly noninfective. If pretreatment of one of the cells results in its ability to produce and excrete the desired compound, the bacteriophage will be rendered infective once again and will infect the susceptible cell. Infection results in the transfection of a gene also required by the infected cell. The two cell types now cross-feed each other, enabling their growth into a colony which contains the cell also producing the desired compound.

The two cell types involved in this method are referred to as starter and feeder cells. The starter cell is not susceptible to bacteriophage infection. It is auxotrophic for a first metabolite and produces a second metabolite that the feeder cell requires for survival and growth. It does not produce the desired compound unless treated (e.g., by chemical mutagenesis, genetic engineering, transfection, or transformation) in such a way that its total cellular DNA composition is modified. The feeder cell is a bacterial cell susceptible to lambdoid bacteriophage infection. It is auxotrophic not only for the second metabolite but also for a nutrient which is not the same as the first or second metabolite. It also produces the first metabolite that the starter cell requires for growth.

If the feeder or starter cell does not normally excrete the first or second metabolite, respectively, either or both cells can be altered through any technique known in the art to induce excretion, such as genetically altering a strain to endow it with the ability to excrete the metabolite. Mutagenesis may occur via infection and transfection of viral DNA or transformation with other than viral DNA. Alternatively, chemical mutagenesis with N-methyl-N'-nitro-N-nitrosoguanidine, ethyl methanesulfonate, and ultraviolet irradiation (see e.g., Miller (ed.) *Experiments in Molecular Genetics*, (1972) Cold Spring Harbor, N.Y.) can be used.

Starter and/or feeder cells which require metabolites generally have one or more mutations within their DNA which limit or prevent the ability of that cell to produce that metabolite. Preferably, the starter and/or feeder cell includes deletions at one or more regions of DNA responsible for production of that metabolite. Such deletions prevent the starting cell from mutating to lack the requirement of the metabolite. If the DNA is not deleted, that cell must contain preferentially two or more mutations which prevent production of the metabolite, and do not mutate to produce a cell with an ability to produce a metabolite (i.e., revert) at a frequency of greater the $10^{-10}$ per cell division. Since the mutation rate at any particular nucleotide is between $10^{-3}$ and $10^{-10}$, it is preferable that starter and feeder cells contain at least three mutations within any genes encoding enzymes for the synthesis of the metabolite. The appearance of "false positives" or colonies appearing as a result of something other than that which is desired, is thus avoided.

If the feeder cell is supplied either with the nutrient it lacks, or the means of producing the nutrient, a two-way symbiotic relationship can be established between the starter and feeder cells, resulting in the growth of a colony including both cell types. One way in which the nutrient can be supplied is by transfecting the feeder cell with a gene encoding the nutrient or a polypeptide required for its synthesis. Transfection can be accomplished by the infective lambdoid bacteriophage described above.

To determine appropriate cell pairings the growth requirements of each individual cell type can be compared. For example, The American Type Culture Collection (ATCC) publishes the *Catalogue of Bacteria and Bacteriophages*, (7th ed., 1989) which lists hundreds of compounds that are produced or required by numerous genera. This list can be used to define a pair of strains in which one strain produces something the other strain requires for growth. One of the strains can then be altered through techniques known in the art to require another metabolite for growth, as described. A screening for the desired compound can then be set up. If there is no selectable drug resistance to distinguish the strains, they can be separated based on auxotrophic requirements. Listings of other cultured prokaryotic and eukaryotic cells are available to prepare other pairings. (See, e.g., *Catalogue of Cell Lines and Hybridomas* (7th Ed.) American Type Culture Collection, 1992).

Alternatively, the starter or feeder cell may include mutations which provide a selectable phenotype, for example, resistance to an antibiotic or inability of that cell to grow on a carbon source on which the other cell may grow. The selectable phenotypes allow later separation of the starter and feeder cells from one another. The starter and/or feeder cell may include DNA which has been inserted into those cells by recombinant DNA technology, for example, the treated starter cell may include heterologous genes (i.e., genes from another organism) for the production of the desired compound.

Generally, the feeder cells are able to survive or divide very slowly for only a very limited number of times in the absence of the required second metabolite and nutrient. For example, a bacterial feeder cell may have a rate of cell division of less than one cell division in three hours at 37° C. in growth medium lacking the required metabolite and nutrient but otherwise having all required compounds. This compares to a rate of cell division of 1 in 30 minutes when the feeder cell is provided with the metabolite and nutrient. The rate of cell division of plant and animal cells, or of cells grown under less optimum conditions, may be much lower. It is important in the invention that the feeder cell have a greatly reduced rate of cell division in the absence of the second metabolite and nutrient compared to its rate of cell division in the presence of the metabolite and nutrient. Thus, in the presence of the metabolite and nutrient, its rate of cell division is enhanced (e.g., at least three-fold and most preferably at least ten-fold); production of the first metabolite required by the starter cell is also enhanced in the presence of the second metabolite.

Similarly, the starter cell requirement for the first metabolite produced by the feeder cell need not be absolute. The absence of such metabolite need only significantly reduce the rate of cell survival or division (i.e., by at least three-fold, preferably ten-fold). More importantly the starter cell must produce only a limited amount of the second metabolite in the absence of the first metabolite. Thus, both the starter cell and the feeder cell will grow, survive, and divide only very poorly in the absence of each other and the nutrient, or in the absence of the nutrient and the first and second metabolites. That is, both the starter cell and the feeder cell are dependent upon each other for growth and have a mutual, two-way symbiotic growth relationship.

The first and second metabolites can be any compound which affects the survival and division of the starter and feeder cells. Generally, such desired compounds are chosen from cellular building blocks, e.g., lipids, fatty acids, vitamins, amino acids, nucleic acid components, cytokines, cofactors, and growth factors such as fibroblast growth factor, an interleukin such as interleukin-1 or -2, or any other equivalent compound.

The first and second metabolites also include all products that are able to convert, either directly or indirectly, a non-essential compound of the symbiosis. This definition includes all enzymes that are capable of producing, directly or indirectly, an essential nutrient from existing or added non-essential components of the growth media.

An example of such an enzymatic product is a racemase, which is secreted by an *E. coli* strain. Racemase acts on the D-amino acid, converting it to the L-isomer which is required for growth by the starter cells. Formation of the L-amino acid establishes the symbiosis between the starter and feeder cells.

In the method of the invention, the starter cell is treated so as to increase the probability that it will excrete the desired compound. Treatment of the starter cell includes mutagenizing the starter cell with a chemical or physical mutagen (see, e.g., Miller (ed.) *Experiment In Molecular Genetics*, (1972) Cold Spring Harbor, N.Y.). In another instance, the starter cell is treated by transfecting or transforming it with a vector containing a gene encoding, or involved in the production of, the desired compound (see, e.g., Sambrook et al. (eds.) *Molecular Cloning:A Laboratory Manual* (1989) Cold Spring Harbor, N.Y.).

Alternatively, treatment includes genetically engineering the starter cell to express a mutator gene. Such forms of mutation result, in some embodiments, in a rate of mutation of at least $10^{-6}$ per nucleotide base per cell division. Mutator genes are well known to those of ordinary skill in the art. Generally, they are mutations in a DNA polymerase which causes that polymerase to incorporate nucleotide bases incorrectly. Such incorrect incorporation results in a mutation. Generally, such mutator genes can increase the mutation rate of a cell by between 1000- and 100,000-fold. The mutation rate of any particular cell can be readily measured by one of ordinary skill in the art, for example, by providing a plasmid comprising the lacZ gene of *E. coli* and measuring the rate of mutation of nucleotide bases within the lacZ gene. It is preferred that the rate of mutation be at least $10^{-6}$ per nucleotide base, preferably at least $10^{-4}$ per nucleotide base, in order to allow rapid mutation of DNA of the starting cells. Because of the presence of such mutator genes within the starter cell, and as discussed above, it is preferable that the genes encoding the metabolite be deleted so that the chance of reversion is practically zero. If other genes mutate to replace the lost function, those genes could either be deleted, mutated or modified to remove the interference.

In one example of the method of the invention, a starter cell can be treated to include a mutator gene such as mutD, for example, which increases the frequency of spontaneous mutation up to about $10^5$ (Kornberg et al. (1991) *DNA Replication* (2d ed). W. H. Freeman, N.Y. p. 172). Also included in the starter cell is a mutation conferring resistance to streptomycin (rpsL); this resistance allows ready purification of the starter cell, and its descendants from the feeder cell (which is sensitive to streptomycin) by growth in a medium containing streptomycin. In addition, the starter cell includes a mutation such that the starter cell requires an amino acid for growth. This amino acid must be provided by the feeder cell.

The feeder cell is blocked for the synthesis of the second metabolite, which, in this example, is a vitamin such as biotin. The starter cell secretes this vitamin during growth in the presence of the required amino acid. The feeder cell has a mutation which results in the overproduction of the amino acid required for growth by the starter cell. The feeder cell is lacking functional genes required for the synthesis of an amino acid other than the first metabolite (e.g., tryptophan) and for its utilization of lactose (lac) which allows selection against growth of the feeder cell, even without the use of antibiotic streptomycin. Therefore, the feeder cell population cannot be grown on a medium employing lactose as a carbon source for cell growth. The starter cells can grow on this medium. Such medium may also contain streptomycin to ensure growth of starter cell in favor of the feeder cell The feeder and starter cells are cultured in the presence of a lambdoid bacteriophage carrying a gene for tryptophan which the feeder cell requires. If a change in the total cellular DNA in the starter cell has occurred (e.g., by chemical mutagenesis, genetic engineering, transfection, or transformation), resulting in the production and excretion of a desired compound, the surrounding feeder cells will grow. The faster such feeder cells produce the first metabolite required for growth of the starter cell, the faster the starter cell will grow and provide the second metabolite needed for the growth of the feeder cell. A colony is thus formed including the mutant starter cells, some of which are producing the desired compound, and the feeder cells.

If the cell density in the initial screening is high, as is the case if a rare mutation is looked for, the resulting colony will be a mixture of starter cells, mutant starter cells, and feeder cells. A further round of symbiotic screening using a lower initial cell density can be performed to isolate a pure population of mutant starter cells producing the desired compound from the colonies.

In the method of the invention, a plurality of starter cells treated as described above and feeder cells are cultured together on the solid growth medium in the presence of a reversibly noninfective, modified lambdoid bacteriophage. Useful lambdoid bacteriophage include all lambda-related bacteriophages and all derivatives, genetically engineered derivatives, and hybrids thereof, such as, but not limited to, Φ80, Φ81, bacteriophages 21, 82, 424, 432, λimm43, λimm21, phagemids, λEMBL, and λgt.

This lambdoid bacteriophage has a reduced or no capacity for lytic infection. In some embodiments, this reduced capacity or incapacity is the result of a mutation in the virus, such as the CI857 mutation resulting in the temperature sensitive expression of the CI lambda repressor, thereby enabling lytic infection only at certain temperatures which do not include the temperature at which the starter and feeder cells are cultured. Such a bacteriophage is called a temperate bacteriophage. The bacteriophage of this invention also carries, in its genome, a gene required by the feeder cell for growth. One such example is the trpE gene which can alleviate the tryptophan requirement of an *E. coli* trpE strain.

To construct λtrpE CIts857, both λEMBL3 DNA and λCIts857 DNA were digested with NheI and the large fragment from λEMBL3 and the small fragment from λCIts857 were isolated by electrophoresis in agarose (Maniatis et al. (1982) *Molecular Cloning: A Laboratory Manual*, Cold Spring Harbor Laboratory, Cold Spring Harbor, N.Y. pp. 150–170). The isolated fragments were ligated using T4 DNA ligase and the resulting DNA was packaged in vitro. The resulting bacteriophage were used to infect *E. coli* and a bacteriophage stock was prepared from the infected *E. coli* (Davis et al. (1980) *Advanced Bacterial Genetics*, Cold Spring Harbor Laboratories, Cold Spring, N.Y. pp.74–77).

One type of lambdoid bacteriophage, the bacteriophage lambda, consists of an icosahedral head or capsid with a radius of 30 nm and a flexible tail 150 nm long ending in a tapered basal part and a single tail fiber (FIG. 1A). The genome of the bacteriophage is linear DNA. This DNA is found in the capsid head and has cohesive ends, the right one of which (as defined by the genetic map) protrudes into the upper third of the tail. The tail consists mainly of a tube of 32 disks each consisting of six gpV proteins, the products of the V gene.

In the present invention, a lambdoid bacteriophage is genetically or chemically modified so as to expose a target molecule on the outer surface of its tail (FIG. 1B). This can be accomplished in the genetically modified phage by providing a truncated gene which encodes at least the amino terminal two-thirds of a lambdoid major tail protein such as, but not limited to, the gpV protein, or other major lambdoid tail protein, and linking this gene fragment to a gene encoding a target protein, thereby forming a gene fusion. The protein product of the gene fusion, i.e., a protein construct, may be expressed in a bacterial cell where it, along with the other bacteriophage components, is assembled into a lambdoid bacteriophage if genes encoding the other viral components and enzymes required for bacteriophage assembly are present.

Figure 6A:
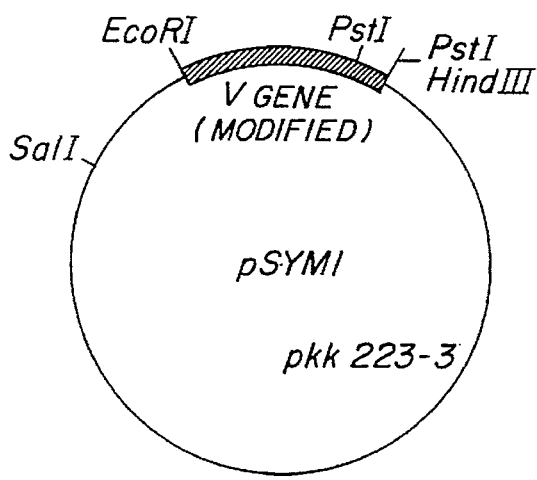
FIG. 6A is a schematic representation of the pSYM1 plasmid containing the PCR fragment of FIG. 4.
Figure 6B:
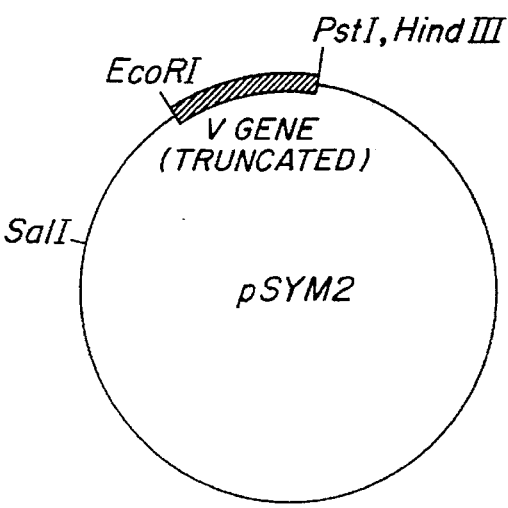
FIG. 6B is a schematic representation of plasmid pSYM2 containing a truncated V gene with multiple cloning sites.
Figure 6C:
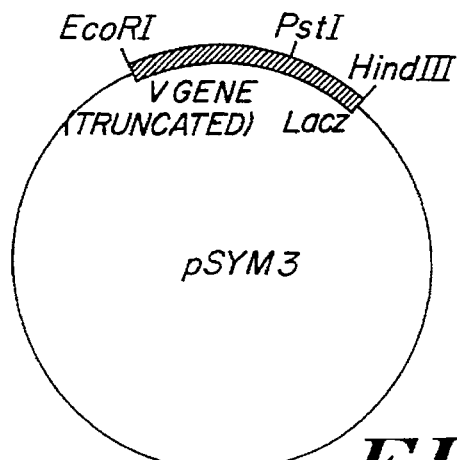
FIG. 6C is a schematic representation of plasmid pSYM3 containing a truncated V gene and a gene encoding a marker protein.
Figure 5:
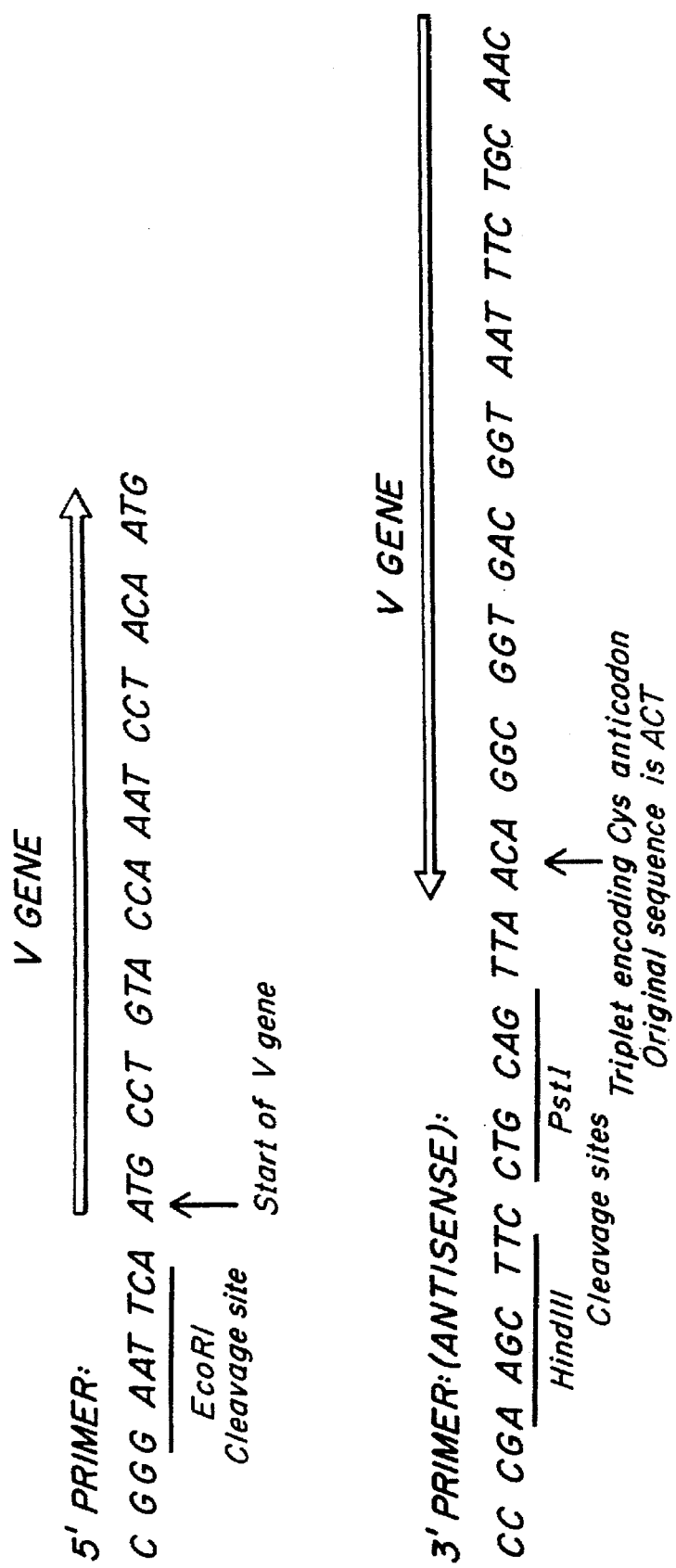
FIG. 5 is a schematic representation of the 3' and 5' primers used to provide the PCR fragment containing the full length, modified V gene in plasmid pSYM1.

The gene fusion may be prepared as follows. The nucleic acid sequence of the V gene is known (Sanger et al. (1982) *Mol. Biol.* 162:729) and as set forth in the Sequence Listing as SEQ ID No: 2 and in FIG. 2. This gene is simultaneously cloned and modified by PCR methods (Scharf, "Cloning with PCR" in PCR Protocols. *A Guide to Methods and Applications* (Innis et al., eds.) Academic Press, San Diego, Calif. (1990) pp.84–91), resulting in a full length V gene with its carboxy terminal Ser$^{246}$ codon replaced with a Cys codon TGT (FIG. 3). The primers used for PCR are set forth in SEQ ID Nos.: 4 and 5 and are shown in FIG. 5. The amino acid sequence of this modified gpV protein is also shown in FIG. 3 and in SEQ ID No: 3. The modified V gene has been cloned into an expression vector (pKK223-3, Pharmacia, Piscataway, N.J.) resulting in the pSYM1 plasmid shown in FIG. 6A. When pSYM1 is digested with PstI (New England Biolabs, Beverly, Mass.) and religated using T4 DNA ligase (New England Biolabs, Beverly, Mass.), the pSYM2 plasmid shown in FIG. 6B is obtained. This digestion results in the loss of nucleic acid encoding the C-terminal 24 amino acids of the gpV protein and its replacement by nucleic acid encoding the hexapeptide Ser-Phe-Cys-Phe-Gly-Gly (set forth in the Sequence Listing as SEQ ID NO: 8) as depicted in FIG. 4. Of course, the plasmid may be designed such that it may be digested with other restriction endonucleases in the alternative or as well, resulting in the loss of other gpV protein amino acids.

Plasmid pSYM2 has a unique PstI cleavage site near the 3' terminus of the truncated V gene. The target molecule encoding gene to be fused with the V gene is isolated using the PCR strategy employed for the cloning of the V gene. In this strategy, PCR primers that contain PstI restriction sites are employed to obtain a PstI fragment containing the gene-to-be-fused. This fragment is then ligated to the PstI site in pSYM2 using T4 DNA ligase. This approach requires that there be no PstI site present in the gene-to-be-fused.

When the target molecule gene contains a PstI site, a restriction enzyme that produces blunt ends is used instead of PstI, provided its recognition sequence is not present in the coding region. Such enzymes include BsaAI, Bst1107I, DraI, Eca136II, Eco47III, EcoRV, and EheI.

After digesting the pSYM2 plasmid with PstI, the PstI site is converted to a blunt end using T4 DNA polymerase. (Maniatis et al., *Molecular Cloning: A Laboratory Manual* Cold Spring Harbor Laboratory, Cold Spring Harbor, N.Y. (1982) p. 395). Of course, other restriction endonucleases with single recognition sites may be used as well. The gene for the target molecule is then ligated into the plasmid using T4 DNA ligase.

A fragment of another gene encoding at least an antigenic portion of a third protein can be incorporated into the plasmid in a position such as, but not limited to, a position distal to the V gene, resulting in a plasmid such as pSYM3 (FIG. 6C). The third protein may be a marker protein such as β-galactosidase (encoded by the lacZ gene), chloramphenicol acetyltransferase, or alkaline phosphatase, among others. Inclusion of the third protein alleviates the need of obtaining antibodies to the target molecule since antibodies to the third protein can be used to inactivate the bacteriophage. Thus, using the same PCR methodology describe above, a V/target/lacZ gene fusion can be prepared which encodes a gpV/target molecule/β-galactosidase or protein construct.

The plasmid pSYM3 (FIG. 6C) is an example of such a plasmid where the gene encoding the target molecule is closed between the V gene and a fragment of lacZ. Transcription and translation of this unit results in the production of a gpV/target/β-galactosidase fusion protein. The plasmid pSYM3 is constructed from pSYM2 as described above where the aforementioned gene-to-be-fused is a 500 bp fragment of lacZ beginning at the ATG start codon of the gene. The primer used to anneal to the 5' end of the gene fragment (SEQ ID NO: 9) contains a PstI recognition site, and the primer used for the 3' end (SEQ ID NO: 10) contains a HindIII restriction site. This results in the formation of a V gene/lacZ gene fusion which still contains a unique PstI restriction site into which the gene encoding the target molecule can be cloned.

In addition to incorporating a third protein into the C-terminus of the fusion protein, synthetically derived peptides may be incorporated. The plasmid, pSYM27, is one such example where, in a similar fashion to the incorporation of a β-galactosidase fragment, a 10 amino acid sequence termed Strep-tag (Schmidt et al. (1993) *Protein Engin.* 6:109–122) (SEQ ID NO: 11) is attached to the C-terminus the modified V gene present in pSYM1. Plasmid pSYM1 is digested with the restriction endonucleases HpaI and HindIII, which recognize the nucleotide sequences GTTAAC and AAGCTT respectively. A synthetic DNA segment encoding the Strep-tag peptide is ligated to the digested pSYM1, resulting in the plasmid pSYM27. The synthetic DNA segment is made by annealing the two oligonucleotides (SEQ ID NO: 12 and 13) shown in FIG. 11. The cloning strategy and resulting plasmid, pSYM27, are shown in FIG. 12.

In the case of a genetically modified bacteriophage, the target molecule can be any protein, polypeptide, or peptide which is translated from a known nucleic acid sequence and which can be peptide bonded to the carboxy terminal end of the truncated gpV protein without abolishing virus assembly or infectivity. Such target molecules include, but are not limited to proteins such as enzymes (e.g., beta-lactamase, triose phosphate isomerase, or hexokinase) enzyme substrates (e.g., pre-interleukin-1, proinsulin, preproinsulin, or erythropoietin) Immunoglobulins, or portions thereof (e.g., Fv, Fab, or $(Fab')_2$), receptors or portions thereof (e.g., the estrogen receptor or the insulin receptor), ligands (e.g., ciliary neuronotrophic factor or luteinizing hormone), cytokines (e.g., macrophage migration inhibition factor or the interleukins), growth factors (e.g., fibroblast growth factor or granulocyte colony stimulating factor) and toxins (e.g., pertussis toxin or botulinum toxin).

When constructing the gene fusion, the process often results in or requires the inclusion of extraneous DNA sequences that, when transcribed and subsequently translated, result in the inclusion of extraneous additional amino acids in the gene fusion product. These additional amino acids may be located between any of the component genes of the construct.

To obtain the genetically modified lambdoid bacteriophage of the invention, the gene fusion encoding the protein construct is provided in a plasmid which is used to transform a bacterial cell such as *E. coli* that can be infected by the bacteriophage. Alternatively, this cell may be preinfected with bacteriophage having nonfunctional gpV protein prior to transformation with the plasmid. The cell is then induced to produce modified bacteriophage by chemical stimulation (e.g., with IPTG) and temperature shifting to a high growth temperature (e.g., about 42° C.). This results in mass production of phage and eventual cell lysis. Cellular debris may be removed by centrifugation resulting in a cell-free λ lyate.

When a temperature sensitive derivative of bacteriophage lambda is employed (e.g., CIts), the ratio of gpV protein to modified gpV protein can be regulated to some extent by varying the time between plasmid (and hence modified gpV protein) expression and bacteriophage (hence gpV protein) expression. Expression of modified gpV is inducible by addition of IPTG. CIts derivatives of bacteriophage lambda are also inducible upon temperature shifting (Maniatis et al., in *Molecular Cloning: A Laboratory Manual*, Cold Spring Harbor Laboratories, Cold Spring Harbor, N.Y. (1982) pp. 78–79). IPTG induction followed by a temperature shift upward to 42° C. leads to cell lysis and the release of bacteriophage lambda containing modified gpV.

Genetically modified phage may also be assembled in vitro as described below for chemically modified phage.

Chemical modification of the bacteriophage so as to expose a target molecule on the outer surface of its tail can be accomplished by chemically linking the target molecule to a genetically modified gpV protein, and then assembling the bacteriophage in vitro using this protein construct instead of or in combination with gpV protein.

The altered gpV protein starting material has relatively non-reactive native amino acid residue(s) replaced with chemically reactive amino acid residues. Such chemically reactive amino acid residues include histidine, cysteine, tyrosine, and tryptophan. These reactive amino acid residues may be located anywhere throughout the sequence of the gpV protein and more than one amino acid residue may be replaced with such a reactive residue. Cysteine is the preferred reactive amino acid residue because there are no cysteine residues present in the native gpv protein sequence, and this residue can be selectively modified. The native sequence also contains no histidine residues, but does have five tyrosine residues and six tryptophan residues. For example, SEQ ID NO: 3 in the Sequence Listing sets forth the amino acid sequence of a gpV protein in which the carboxy terminal serine residue at position 246 has been replaced with a cysteine residue (FIG. 3). This altered gpV protein can be prepared as follows.

The plasmid pSYM1 is used to transform *E. coli*. The transformed strain is induced (Sambrook et al. in *Molecular Cloning: A Laboratory Manual* (1989) p.17.13. Cold Spring Harbor Laboratory, Cold Spring Harbor, N.Y.), then lysed as a source of modified gpV protein. If necessary, the gpV protein can be purified further as described by Katsura et al. (*Virol.* (1977) 6:129).

Partially purified, genetically modified gpV protein is then chemically coupled to a selected target molecule to form the protein construct. The target molecule can be any molecule that can be linked to the modified gpV protein via its reactive amino acid residue(s) without abolishing phage assembly or infectivity. Such target molecules include proteins, peptides, carbohydrates, hormones, glycoproteins, proteoglycans, lipoproteins, proteolipids, lipids, lipopolysaccharides, toxins, cofactors, nucleic acids, glycolipids, terpenes, antibiotics, or vitamins. Useful target proteins include immunoglobulins or portions thereof (such as Fab, Fv, (Fab')$_2$), receptors or portions thereof (such as the estrogen receptor and the insulin receptor), ligands (such as ciliary neuronotrophic factor and luteinizing hormone), enzymes (such as beta-lactamase, triose phosphate isomerase, and hexokinase), enzyme substrates (such as pre-interleukin -1, proinsulin, and erythropoietin), cytokines (such as macrophage migration inhibition factor and the interleukins), growth factors (such as fibroblast growth factor and granulocyte colony stimulating factor), or toxins (such as pertussis toxin and botulinum toxin A).

Coupling of the target molecule to the gpV protein may be accomplished method known in linkage method known in the art, such as covalent bonding. For example, the sulfhydryl group in a cysteine residue of the gpV protein and a sulfhydryl group in any cysteine residues present in the target molecule may be oxidized to form a disulfide bond between them. The target molecule instead can be chemically reacted with the imidazolyl group in histidine, the hydroxyl group in tyrosine, or the indoyl group in tryptophan.

The target molecule may be chemically cross-linked to the reactive amino acid residue of the gpV protein. Cross-linking can be accomplished using any number of known cross-linking reagents, such as those set forth in U.S. Pat. No. 5,112,615, herein incorporated by reference. One type of useful cross-linking reagent is a bifunctional reagent such as β-maleimidopropionic acid N-hydroxysuccinimide ester which can be employed according to methods known in the art (e.g., *Laboratory Techniques in Biochemistry and Molecular Biology*, Elsevier Science Pub. Co., Amsterdam (1988) vol. 19).

To obtain the chemically modified bacteriophage of the invention, the protein construct is contacted with other lambdoid phage components and enzymes required to assemble the phage in vitro. Methods of phage assembly are well known in the art (see, e.g., Hohn (1979) *Meth. Enzymol.* 68:299–309). In vitro assembly enables the ratio of unmodified gpV protein to modified gpV protein to be controlled, thus allowing the introduction of a limited number of protein constructs per phage particle.

Lambdoid components and assembly enzymes can be provided in the form of a cell lysate (or packaging extract) from *E. coli* preinfected with lambdoid phage that is defective in a step of morphogenesis. For example, when bacteria infected with a prophage mutant in gene V are induced, precursor phage particles accumulate. Induction may be accomplished by a shift in temperature if the infecting phage has a temperature sensitive genotype such as λV⁻CIts Sam7. To obtain a V⁻derivative of a commercially available lambda phage, such as λC1857Sam7 (New England Biolabs, Beverly, Mass. ), the phage are mutagenized (Katsura (1976) *Molec. Gen. Genet.* 148:31). *E. coli* JM105 (Stratagene, La Jolla, Calif.) carrying the pSYM1 plasmid are infected with the mutagenized phage population. Colonies appearing at 32° C. are replica plated to plates with or without IPTG, which induces gpV production. Colonies which grow on plates without IPTG, but do not grow on plates with IPTG, are selected as a source of V⁻phage. The V gene mutation can be complemented, in vitro, by the addition of the missing gpV protein, which, in this invention, is chemically coupled to a target protein.

The assembled bacteriophage are purified from either the bacterial cell lysate or in vitro system and then rendered non-infective. This may be accomplished by the binding of a molecule to the target molecule on the bacteriophage. Binding stops the bacteriophage from being able to infect a cell. Useful binding molecules include antibodies or binding portions thereof such as Fv, Fab, or (Fab')$_2$ fragments. The production of such antibodies and biochemically or genetically produced fragments is well known in the art (see, e.g., *Antibodies: A Laboratory Manual* (Harlow and Lane, eds.) Cold Spring Harbor Laboratory, Cold Spring Harbor, N.Y. 1988).

Other useful binding molecules include receptors which if necessary may be presented in lipid or detergent micelles or liposomes or on cell surfaces to keep their configuration. Such receptor-containing liposomes and micelles can be prepared using any number of methods known in the art (see, e.g., Georgoussi et al. (1990) *Biochem. Biophys. Acta* 1055:69). When the target molecule is a receptor ligand, the receptor will serve as the immobilizing agent. Receptors which can be presented to the bacteriophage in this way include nicotinic acetylcholine receptor (Chak et al. (1992) *Meth. Enzymol.* 207:546), inositol 1,4,5-triphosphate receptor (Kamata et al. (1992) *J. Biochem.* 111:546), hepatic vasopressin receptor (Georgoussi, ibid.), and the rat ovarian receptor for luteinizing hormone (Kusuda et al. (1986) *J. Biol. Chem.* 261:16161).

Yet other useful binding molecules include all molecules capable of binding to the target molecule in a competitive fashion. When ligands are used as the binding molecule, they must be immobilized as described in the following paragraph.

Alternatively, the bacteriophage can be rendered non-infective by binding it via its target molecule to a matrix. Such matrices include, but are not limited to, commercially available materials such as a gel consisting of dextran cross-linked with epichlorohydrin (e.g., Sephadex™), a special gel prepared from agarose (e.g., Sepharose™), and agarose. When the bacteriophage is immobilized to a matrix it is unable to bind to and infect a cell. In this method the bacteriophage is immobilized to the matrix and thus is unable to enter and infect a cell. Immobilization to the matrix may be accomplished by chemical linkage or by various chemical cross-linking methods (see, e.g. U.S. Pat. No. 5,112,615, herein incorporated by reference, and Wilchek et al. (1984) *Meth. Enzymol.* 104:3). One type of useful cross-linking reagent is a bifunctional reagent such as β-maleimidopropionic acid N-hydroxysuccinimide ester which can be employed according to the method described in *Laboratory Techniques in Biochemistry and Molecular Biology* (Elsevier Science Publishing Co., Amsterdam, (1988), vol. 19).

Figure 7A:
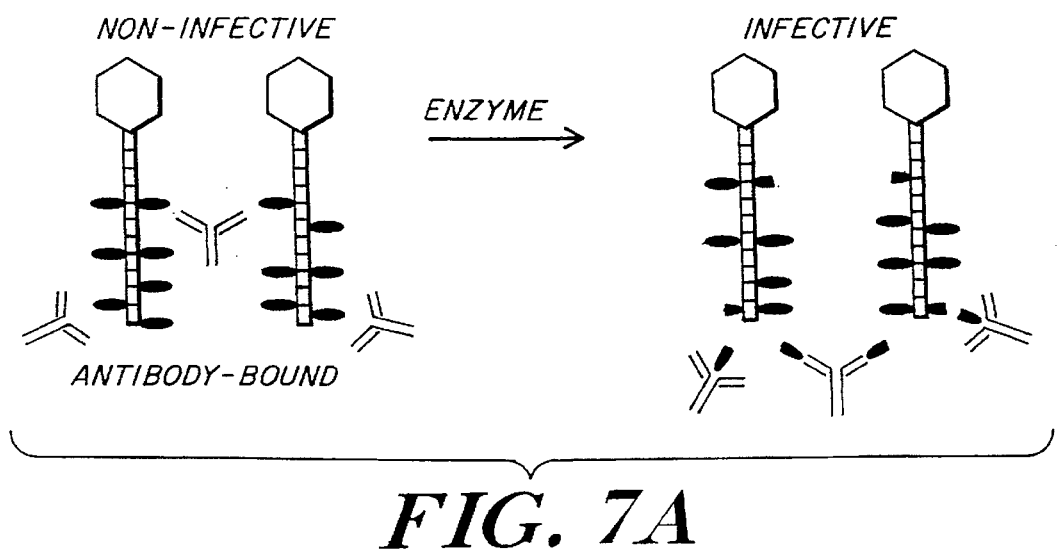
FIG. 7A is a diagrammatic illustration of one method of rendering the noninfective bacteriophage infective using an enzyme.
Figure 7B:
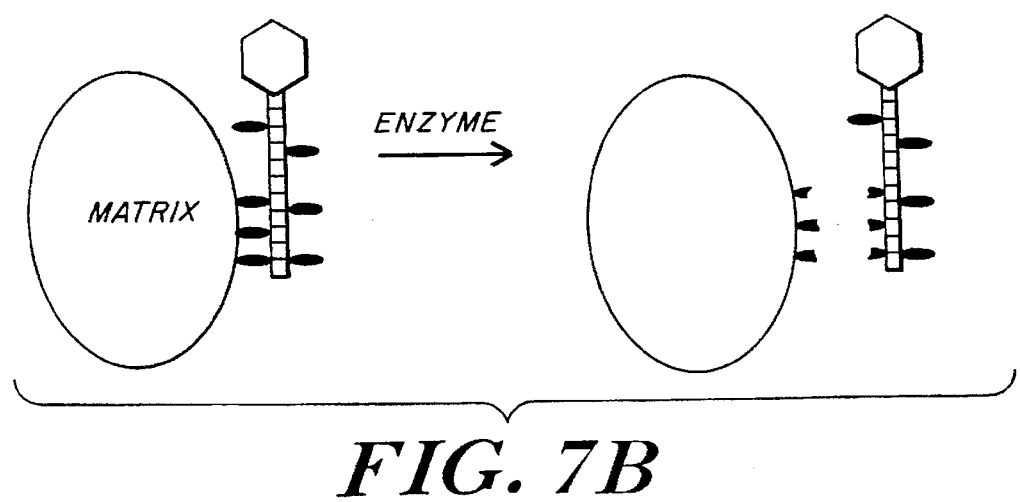
FIG. 7B is a diagrammatic illustration of another method of rendering the noninfective bacteriophage infective using an enzyme.
Figure 7C:
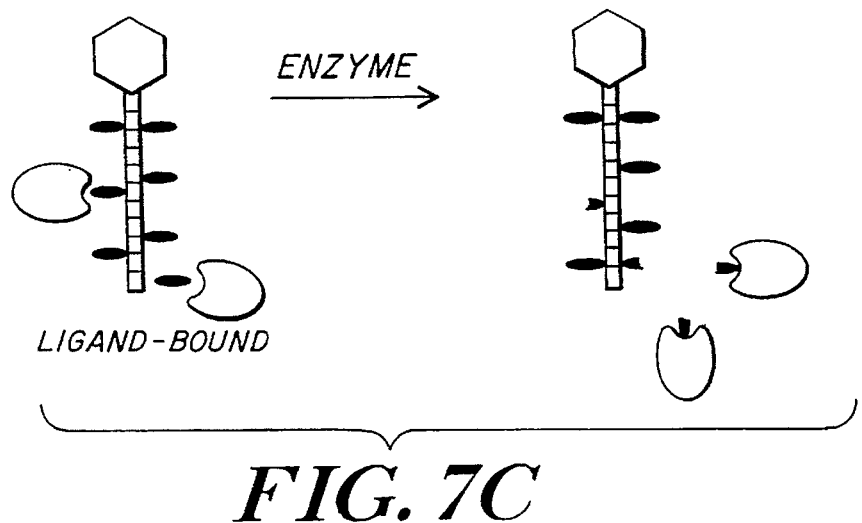
FIG. 7C is a diagrammatic illustration of yet another method of rendering the noninfective bacteriophage infective using an enzyme.
Figure 7D:
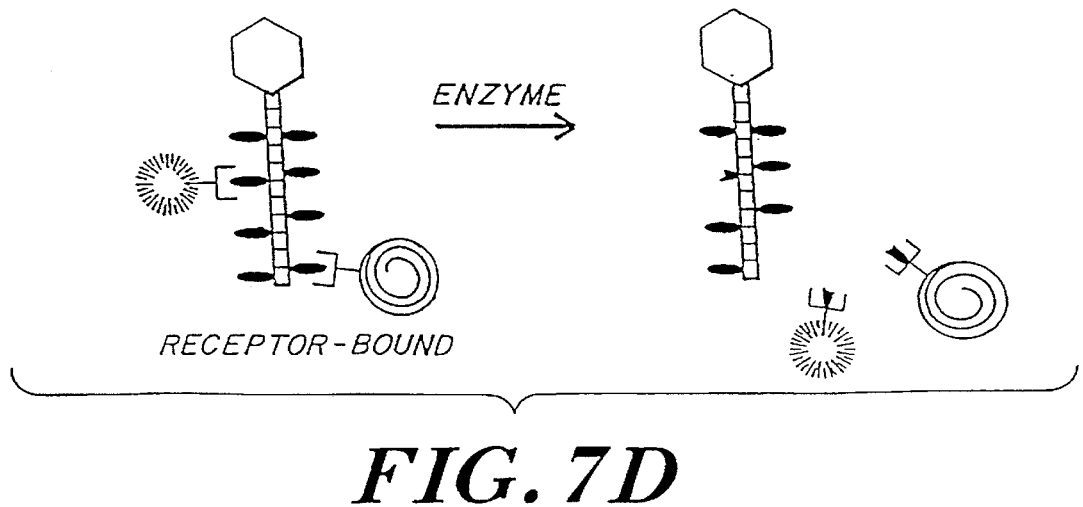
FIG. 7D is a diagrammatic illustration of still another method of rendering the noninfective bacteriophage infective using an enzyme.

The method of the invention has been designed such that the inactivated bacteriophage is released or liberated from the matrix or binding molecule by the desired compound. Thus, if the desired compound is an enzyme, it can be used to liberate non-infective bacteriophage by cleaving target molecule bound to antibodies (FIG. 7A), matrices (FIG. 7B), ligands (FIG. 7C), or receptors (FIG. 7D).

Figure 8A:
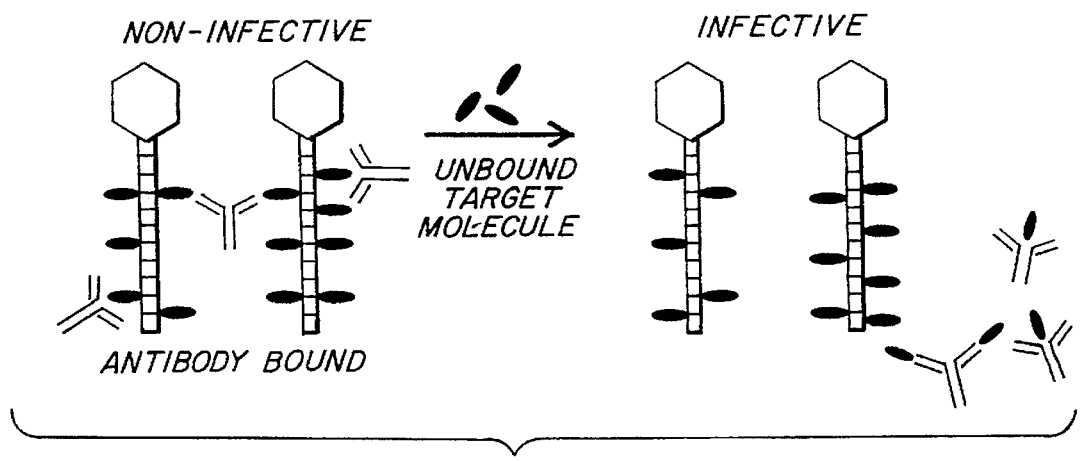
FIG. 8A is a diagrammatic illustration of one method of rendering the noninfective bacteriophage infective using unbound target molecules.
Figure 8B:
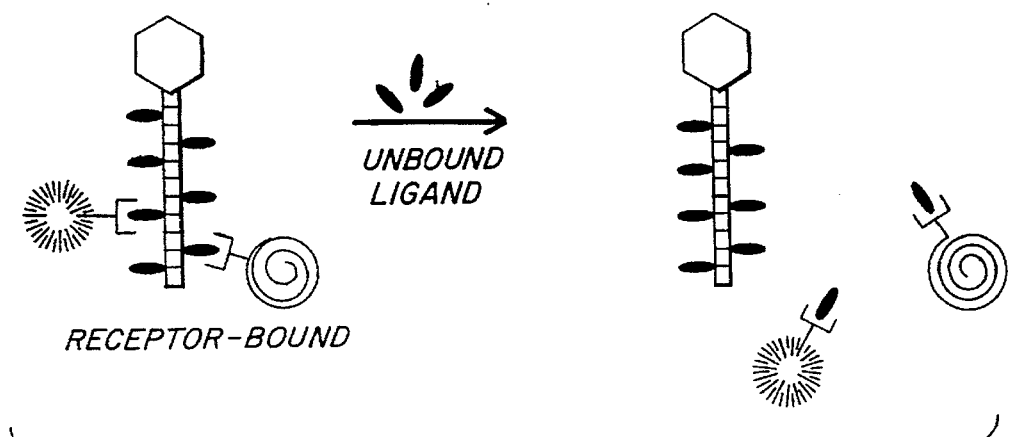
FIG. 8B is a diagrammatic illustration of one method of rendering the noninfective bacteriophage infective using unbound ligand.
Figure 10:
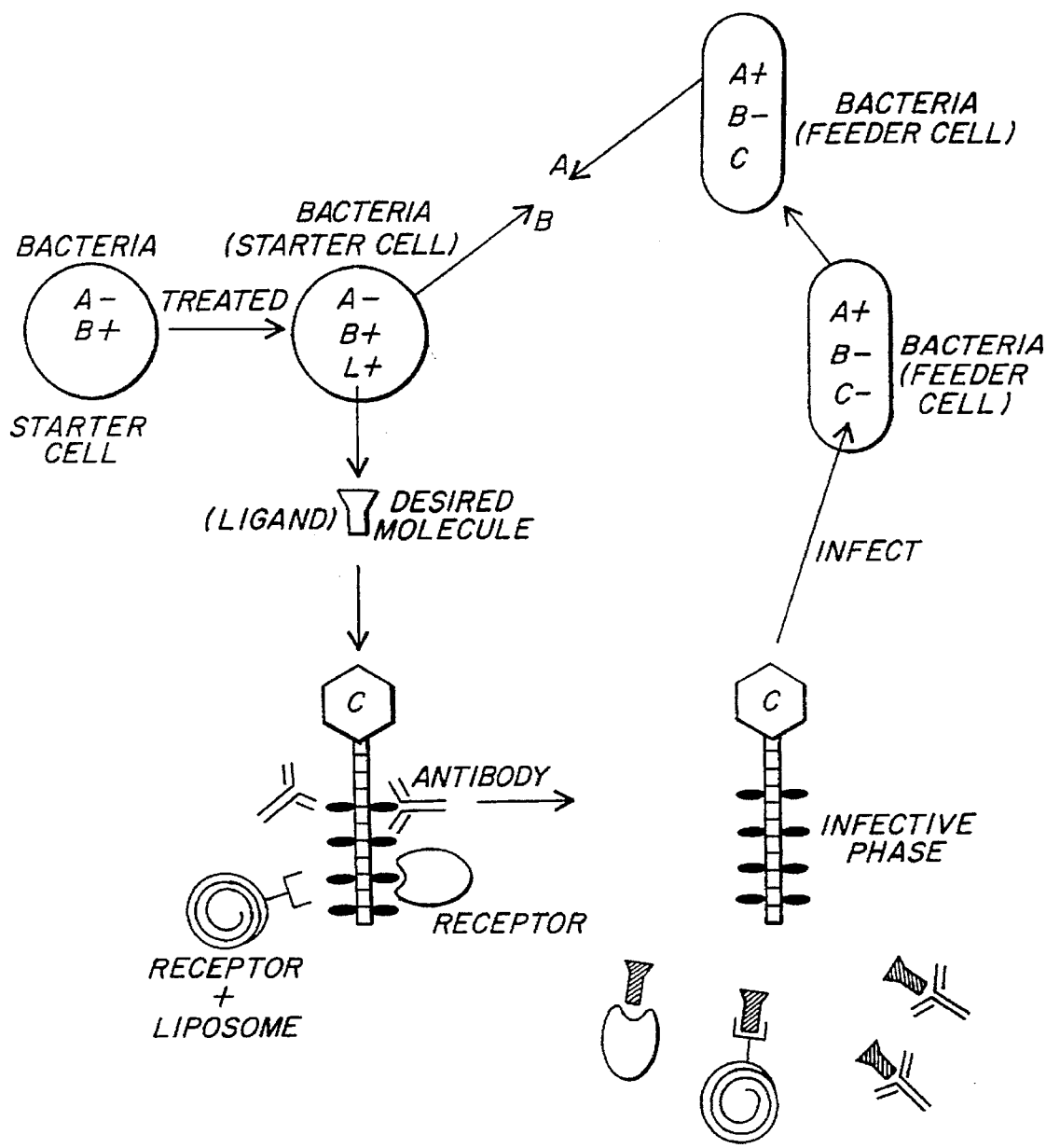
FIG. 10. is a diagrammatic representation of another embodiment of the a method of the invention.

The method of the invention may be used to detect a cell excreting a desired ligand, which is the desired compound (FIGS. 8A, 8B, and 10). In this method, a treated starter cell that produces the desired compound is selected from a population that does not produce the compound. The treated starter cells are cultured with a feeder bacterial strain that is capable of being infected by bacteriophage lambda and requires for growth a gene to be supplied by the bacteriophage. For example, a strain of bacteriophage lambda, such as λ trpE CIts857 described above, which carries both the temperature sensitive repressor CIts857, and a selectable marker gene, trpE (Frischauf et al. (1983) *J. Mol. Biol.* 170:827–842), may be employed to infect a bacterial strain carrying the modified gpV protein.

After IPTG induction of the modified gpV protein, temperature shifting to 42° C. results in the production of lambdoid bacteriophage that carry the gene required for growth by all feeder cells. Either antibodies directed against the target molecule or a cell receptor specific for the ligand are utilized to render the modified bacteriophage non-infective, as described above. The presence of a ligand-(desired compound)-producing bacterial cell causes the release of bacteriophage by providing unbound ligand to which the bacteriophage-linked ligand-bound antibody or receptor can bind instead of the bacteriophage-linked ligand. When the antibody or receptor chooses to bind with the unbound ligand, it releases the bacteriophage enabling it to infect the nearby feeder cell which secretes the metabolite needed by the starter cell. Infection also provides the needed gene to the feeder cell, and thereby endows the feeder cell with the ability to grow. The growing feeder cell excretes the metabolite needed for starter cell growth.

Figure 9:
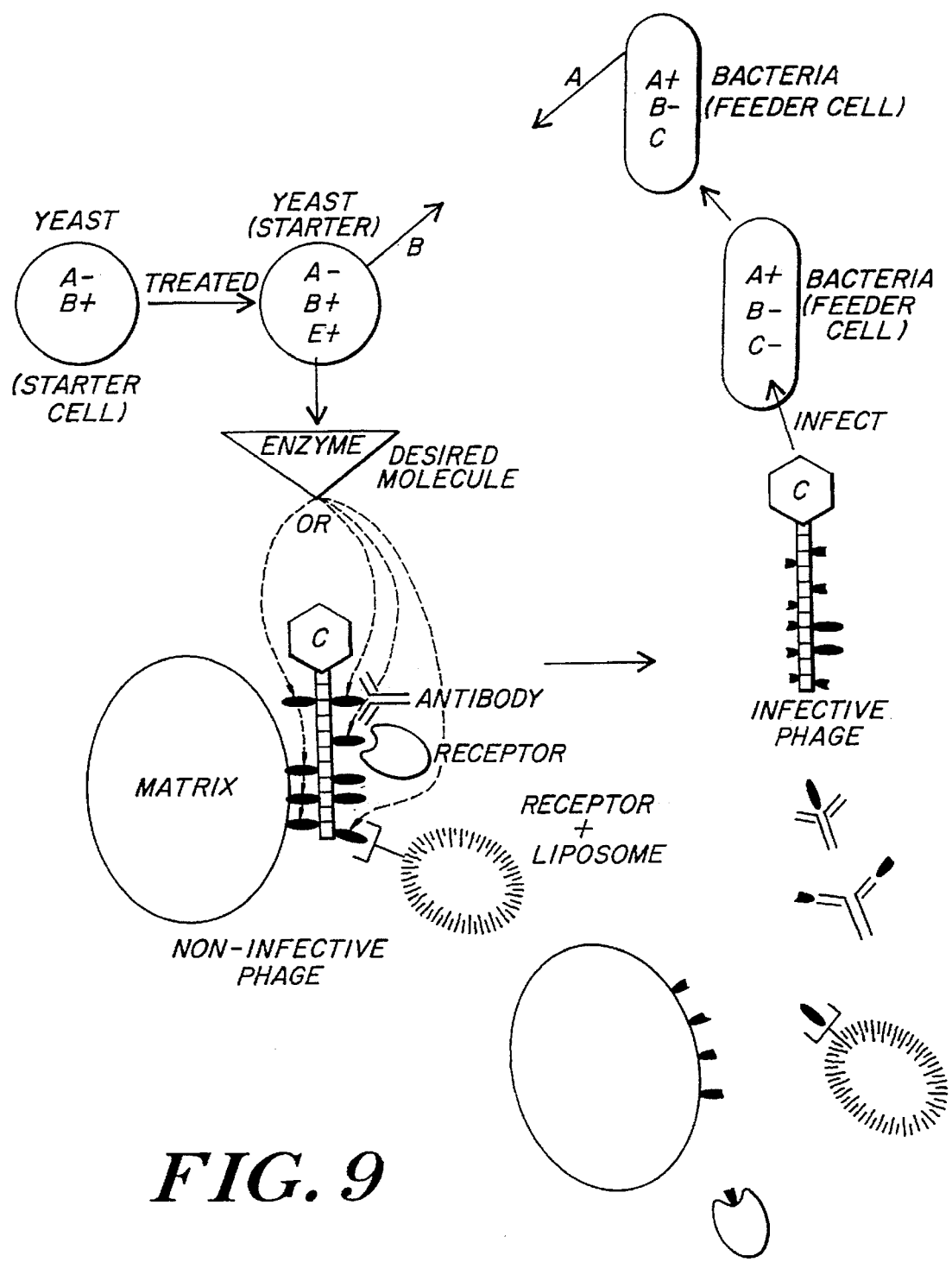
FIG. 9. is a diagrammatic representation of one embodiment of the a method of the invention.

Likewise, the method of the invention may be used to select a starter cell that secretes a desired compound which is an enzyme from a population of starter cells that does not secrete the enzyme. In FIG. 9, this starter cell is exemplified by a yeast cell. This starter cell strain is auxotrophic for a first metabolite and so will grow only if provided with the metabolite by the feeder bacteria. The starter cell also excretes a second metabolite, which the feeder bacteria requires for growth. Additionally, the feeder cell requires for growth a gene present in the bacteriophage genome. In this method, the bacteriophage has a temperature sensitive genotype (e.g., CIts 857) and carries a selectable marker gene may be employed to infect a strain carrying a gene fusion encoding gpV protein modified with an enzyme substrate as the target molecule. After IPTG induction of modified gpV, temperature shifting to 42° C. results in cell lysis and the production of bacteriophage lambda carrying the gene required for growth by all feeder cells. Antibodies directed against either the target molecule (when pSYM2 is employed) or β-galactosidase (when pSYM3 is employed) are used to render the modified bacteriophage non-infective, as described above. Alternatively, the target molecule may be inactivated by immobilization to a matrix or receptor. If an enzyme-producing cell is present, the enzyme produced by the treated starter cell cleaves the bound, bacteriophage-linked target protein, thereby releasing the bacteriophage and rendering it infective again. The released bacteriophage then infects the feeder cell at low growth temperature, providing it with the gene it needs to survive and grow. The infected feeder cells are now capable of symbiotic growth in the presence of nearby treated starter cells resulting in the formation of colonies containing feeder cells and treated starter cells that excrete the desired compound.

It is important to ensure that the physical diffusion of metabolites and the desired compound in the growth medium is proportionate to the rate of consumption of the metabolites by surrounding cells requiring such compounds. The relative rates of these two processes can be changed so as not to allow excessive concentration of the metabolites in the medium. This can be accomplished by altering the incubation temperature, which has little effect on physical diffusion of a metabolite, but has a significant effect on the growth rate of a cell and thus the consumption of the metabolite by that cell. An optimal temperature can be determined by standard procedure. Alternatively, enzymes or antibodies that inactivate the metabolites may be added to the medium. Finally, analogs that compete with the metabolites may be added to the medium.

The colonies may be grown within or on a surface of the solid growth medium, e.g., agar. In addition, the percentage of agar to liquid within the medium can be altered to reduce the rate of spread of growing cells. Again, optimal conditions for any pair of cells can be readily determined by standard procedure.

On solid media, the mobility of bacteriophage and the diffusion of the desired compound are limited. Only cells expressing the desired compound and their immediate neighbors will be infected, thereby resulting in a colony containing both secreting and non-secreting cells. This limited mobility of the bacteriophage enables the selection of a colony containing one secreting cell out of ten bacteria from a plate which initially contained one producing cell out of 10,000,000 bacteria.

When first starting the cross-feeder selection procedure described above, it may be necessary to provide a small amount of the required metabolite and/or desired compound in order to allow some initial growth of the cells. Such initial growth should be limited to a few cell divisions, sufficient to allow a symbiotic relationship to start.

In order to determine whether any particular cell pair is suitable for use in the symbiotic amplification method, about $10^2-10^3$ treated starter cells and about $10^8$ feeder cells are simply inoculated in the presence and absence of the nutrient. In the presence of the nutrient, each starter cell should grow into a colony. In the absence of the nutrient, no colonies should be detected.

Thus, the invention provides a method for simple selection of desired mutant cells. There is no need for tedious screening of mutated cells to determine whether they contain a desired phenotype. The method automatically selects mutant cells which have the property of excreting desired compounds by enabling growth of these cells into colonies.

These mutant cells can be readily isolated after selection in the method of this invention, and used in standard procedures for production of the desired compound.

The types of starter cells that can be employed in such a screening includes cells belonging to the same or different taxonomical kingdoms, phyla, classes, orders, families, genera, or species. Such cells include all unicellular organisms, such as protists and monera, and any additional eukaryotic cells that can be cultured; the feeder cell must be a bacterial cell capable of being infected by a lambdoid bacteriophage. If two different organisms or cell types are employed, the requirements are that the starter cell is capable of growing on the growth medium suitable for bacterial cell growth.

The invention allows isolation and selection of desired mutant cells without use of a large number of growth dishes. $10^7$ starter cells can be introduced onto one plate with feeder cells and growth of only one mutant cell-containing colony from such starter cells may be readily detected. In addition, the method is adaptable to a wide range of products. The method is also amenable to screening enzymatic activities and does not require the use of radioactive or calorimetric substrates.

Furthermore, the method of the invention enables the engineering of new biosynthetic pathways by recombinant DNA technology, for example, by cloning a gene or set of genes into a plasmid or chromosome and transforming an appropriate cell with that plasmid. This method also can be used to improve such engineered pathways. Since different species of microbial cells, and even plant or animal cells, can be used in this method, the method can be used to create mutant cells which produce almost any desired compound. Such cells can be genetically altered to allow selection of mutants that excrete a compound which is not a normal cellular component of that cell. Thus, for example, cells can be engineered to produce a growth factor, such as fibroblast growth factor (FGF) and overproducing mutants selected by growing those starter cells which excrete FGF in the presence of feeder cells and bacteriophage that contain FGF as the target molecule and that have been inactivated by binding to α-FGF antibodies. The excreted FGF competes with the antibodies for phage-bound FGF thus releasing some phage. The released phage in turn infect the feeder cells thus setting up a symbiosis between the treated starter cell excreting the FGF and the infected feeder cells resulting in the formation of a colony containing both cell types.

The method of the invention which includes the use of the modified lambdoid bacteriophage offers several advantages over other systems employing bacteriophages such as M13 or T4. First, any target molecule that can be linked to the gpV protein can be employed as long as it does not completely interfere with in vivo or in vitro assembly or the ability of the resulting bacteriophage to infect bacteria.

Second, the method does not result in the death of the infected feeder cell, and thus, it can be used to isolate mutant or genetically engineered cells that excrete a desired compound, unlike the M13 and T4 systems. By using a temperature sensitive lambdoid strain and a bacterial feeder cell population that requires for growth a particular gene product supplied by the bacteriophage, those cells that excrete the desired compound will render infective an inactivated lambdoid bacteriophage which, in turn, will infect the cell, and at lower temperatures enable the cell to grow.

Third, the method can also be used to screen enzyme libraries for clones having the ability to cleave altered substrate. Immobilization of the bacteriophage via the altered substrate enables isolation of strains from a library that contain an enzyme with the altered specificity from the library. This approach differs from M13 systems where fusion proteins have been used to display proteins because those systems display only the desired compound, and thus are not useful for the detection of such molecules. The approach described herein with the lambdoid system is unique in this respect.

Finally, the range of compounds that can be screened is sizeable and include those compounds that are not required for the growth of one of the strains employed in the symbiosis. Desired compounds include all molecules which meet the criteria as set forth in the lambdoid bacteriophage system described herein.

The following examples illustrate the preferred mode of making and practicing the present invention, but are not meant to limit the scope of the invention since alternative methods may be utilized to obtain similar results.

EXAMPLE 1

Screening Treated Bacteria for Production of Ciliary Neurotrophic Factor Using Genetically Modified Bacteriophage λ

A. Construction of Starter Cell

The starter cell, *E. coli* strain CRstart, is derived from *E. coli* C600, a common laboratory strain, via the following route: C600→CR41→CR46→CR150 →CRstart. CR41 is constructed by selecting spontaneous dehydroproline-resistant isolates of C600. Such isolates overproduce proline (Baich, et al. (1964) *Biochim. Biophys. Acta* 104:397–404). CR46 is constructed by P1 transducing the thr43:Tn10 chromosomal region from CR45 into CR41. CR45 has been described (Wagner (1986) *Mol. Biol.* 191:39–58). CR150 is constructed by selecting for chlortetracycline resistance which results in the loss of the Tn10 (Maloy et al. (1981) *J. Bacteriol.* 145:1110–1111). CRstart is constructed by P1 transducing the lamB:Tn5 containing chromosomal region from GS20 into CR150 using the protocol described by Miller ((ed.) *Experiments in Molecular Genetics* (1972) Cold Spring Harbor, N.Y., pp. 201–205). GS20 is available from the *E. coli* Genetic Stock Center (Department of Biology, Yale University, P.O. Box 6666, New Haven, Conn. 06511-7444). The presence of the lamB allele renders the cell resistant to bacteriophage λ infection. The resulting strain, CRstart, overproduces proline, is resistant to bacteriophage lambda infection, and requires threonine for growth. In addition, the strain requires leucine for growth.

B. Construction of Feeder Cell

The feeder cell, *E. coli* strain CRfeed, is derived from *E. coli* JM109, a common laboratory stain, via the following route: JM109→CR84→CR89→CR151→CRfeed. CR84 is constructed by curing JM109 of the F' factor using acridine orange (Miller (ed.) *Experiments in Molecular Genetics* (1972) Cold Spring Harbor, N.Y., pp. 104–106). CR86 is constructed by P1 transducing the zjj202::Tn10 chromosomal region of CR69 into CR84. CR69 is constructed by P1 transducing the Tn10 region from ATCC Accession No. 47032 (American Type Culture Collection, Rockville, Md.) into ATCC#21277. CR89 is constructed by selecting for chlortetracycline resistance as described above. CR151 is constructed by P1 transducing the trpE chromosomal region from CR76 into CR89. CR76 is constructed by P1 transducing pyrF::Tn5 from GB535 into PLK831 both of which are available from the *E. coli* Genetic Stock Center (New Haven, Conn.). CRfeed is constructed from CR151 by P1 transducing hflA::Tn10 from Y1089 into CR151. Y1089 is a common laboratory strain. The resulting strain, CRfeed, overproduces threonine, is susceptible to bacteriophage λ infection, requires both proline and tryptophan for growth and contains an hflA allele which increases the likelihood that phage infection will lead to lysogen formation.

C. Construction of Bacteriophage λCI857TrpE$^+$

DNA from bacteriophage λgt11 and λEMBL3 (both available from Promega Corporation, Madison, Wis.) are digested with BamHI (New England Biolabs, Beverly, Mass.). Digestion of λgt11 produces a 20 kb, 11 kb, 6.8 kb and a 5.5 kb fragment and digestion of λEMBL3 produces a 20 kb, 13 kb and an 8 kb fragment. The 11 kb fragment from λgt11 are mixed with 20 kb and 13 kb fragments from λEMBL3 and the fragments are ligated together using T4 ligase (New England Biolabs, Beverly, Mass.). The ligation reaction is packaged into phage particles using Packagene® Lamda DNA Packaging System (Promega Corporation, Madison, Wis.). E. coli strain JM109 is infected with the resulting phage and a lysate is prepared as described by Sambrook et al., ((eds.) Molecular Cloning: A Laboratory Manual (1989) Cold Spring Harbor, N.Y., pp. 2.60–2.76).

D. Production of Genetically Modified Bacteriophage Containing the Target Molecule, Ciliary Neurotrophic Factor The gene encoding ciliary neurotrophic factor (CNTF) has been cloned, expressed in chinese hamster ovary (CHO) cells and sequenced (Negro et al. (1991) Eur. J. Biochem. 210:289–294). The entire coding sequence for CNTF is also available from Genbank (Los Alamos, N.Mex.) (accession no. M29828). This gene does not have any PstI recognition sites. The truncated V gene does contain a PstI site near its 3' terminus. A PstI fragment containing the CNTF is obtained by PCR using the 5' primer: GTTGCTGCAGG-TATGGCTTTCATGGAGCATTCA (SEQ ID NO: 6), wherein the underlined sequence is a PstI recognition silte and the double underlined sequence is that of the 5' start of the encoding sequence for CNTF, and the 3' primer: CCGCTGCAGCTACATTTCCTTGTCGTTAG (SEQ ID NO: 7), wherein the underlined sequence is a PstI recognition site and the double underlined sequence is complementary to the 3' end of the coding sequence. Insertion of this PstI fragment into pSYM2 results in the joining of the truncated V gene to the entire CNTF gene. The GT dinucleotide inserted between the PstI recognition site and the beginning of the CNTF coding region is necessary to keep the V gene and CNTF gene in the same open reading frame so that the two genes will be translated into a single polypeptide. This specific dinucleotide was chosen so as to not introduce any extraneous amino acids into the gene fusion product. Competent *E. coli* SCS1 (Stratagene, La Jolla, Calif.) is transformed with the resulting plasmid as described by Hanahan (*J. Mol. Biol.* (1983) 166:557). The transformed strain is induced by IPTG and then incubated with λvir for 15 minutes at 37° C. Top agar is added and the mixture is plated. After 6 hours, the plate is overlayed with lambda dilution buffer (10 mM Tris-HCl, pH 8; 2 mM MgCl 2) and incubated overnight at 4° C. Phage containing CNTF are purified from the resulting lysate by running the lysate over an anti-CNTF antibody column, prepared as described below.

E. Preparation of Anti-CNTF Antibody Column

A column having antibodies directed to the target molecule of the V gene construct is prepared essentially as described in *Antibodies: A Laboratory Manual* ((Harlow and Lane, eds.) Cold Spring Harbor, N.Y. (1988)). Briefly, specific antibodies are mixed with Protein A beads (Sigma Chemical Company, St. Louis, Mo.) using 2 mg of antibody per milliliter of beads. The bead solution is mixed gently for 1 hour at room temperature. The beads are then washed and chemically cross-linked to the antibodies using a bifunctional cross-linking reagent such as dimethylpimelimidate (Sigma Chemical Company, St. Louis, Mo.). Chemical cross-linking is accomplished by shaking the antibody-coated beads for 30 minutes in the presence of 20 mM dimethylpimelimidate. The cross-linking reaction is stopped by washing the beads in 0.2M ethanolamine followed by a two hour incubation at room temperature in 0.2 ethanolamine.

F. Reversible Inactivation of Modified Bacteriophage Using Anti-target Antibodies The CNTF-modified phage are inactivated using anti-CNTF antibodies obtained commercially or by methods well known in the art (see, e.g., *Antibodies: A Laboratory Manual* (Harlow and Lane, eds.), Cold Spring Harbor, N.Y. (1988)) . The appropriate ratio of modified phage to antibody is determined experimentally as described by Oger et al. (*Proc. Natl. Acad. Sci.* (USA) (1974) 71:1554).

G. Treatment of Starter Cell Population

A cDNA library is prepared from rabbit sciatic nerve complementary DNA as described by Lin et al. (*Science* (1989) 246:1023–1025). The starter cell population is transformed and transformants carrying vectors with cDNA inserts are selected as described (Lin et al., ibid).

H. Determination of the Number of Bacteriophage to Use for Screening

Feeder cells and $10^2$ starter are plated with either $10^7$, $10^8$ or $10^9$ bacteriophage λCI857 TrpE$^+$onto minimal A agar plates. The plates are incubated at 30° C. for 24 hours. For screening, the least number of phage that result in all the starter cells growing into visible colonies are utilized.

I. Screening the Treated Starter Cells for Production of CNTF

A population of $10^8$ treated starter cells is plated with $10^8$ feeder cells and an experimentally determined number of inactivated, modified phage. The media is Minimal A (Miller (ed.) *Experiments in Molecular Genetics* (1972) Cold Spring Harbor, N.Y., p. 432) supplemented with glucose. Plates are incubated for 24 hours at 30° C. Only treated starter cells will grow into colonies when cultured LB broth supplemented with ampicillin. A population of $10^2$ cells from this culture are mixed with $10^8$ feeder cells and an experimentally determined number of inactivated, modified phage and the screening is repeated. Colonies are streaked onto LB agar plates supplemented with ampicillin. Resulting colonies produce CNTF.

EXAMPLE 2

Screening Treated Bacteria for Production of Interleukin-1β Converting Enzyme Using Chemically Modified Bacteriophage λ

A. Construction of Bacteriophage λCI857 TrpE$^+$Vam

Construction of bacteriophage λCI857 TrpE$^+$is described in Example 1. Bacteriophage λCI857 TrpE$^+$DNA is digested with ApaI producing a 34 kb and 10 kb fragment. Bacteriophage λVam (Parkinson (1968) *Genetics* 59:311–325 is digested with ApaI producing a 38 kb and 10 kb fragment. The 34 kb fragment from bacteriophage λCI857 TrpE$^+$is mixed with the 10 kb fragment from bacteriophage Vam, and the two fragments are ligated with T4 DNA ligase (New England Biolabs, Beverly, Mass.). The ligation reaction is packaged into phage particles using Packagene® Lambda DNA Packaging System (Promega Corporation, Madison, Wis.). *E. coli* strain Y1089 (Stratagene, La Jolla, Calif.) is infected and packaging extracts are prepared from the infected strain according to Rosenberg et al. (*Gene* (1985) 38:165–175).

B. Construction of gpV/pre-interleukin-1β Fusion

The precursor form of interleukin-1β (pIL-1β) has been cloned into *E. coli* (March et al. (1985) *Nature* 315:641–647). This precursor is isolated from the *E. coli*, using the method of Black et al. (*J. Biol. Chem.* (1988) 263:9437) and chemically cross-linked, through one of its cysteine residues, to the cysteine residue of the modified gpV encoded by pSYM1. The construction of pSYM1 and the method for purifying the modified gpV are set forth in the preferred embodiment. The homofunctional cross-linking reagent bismaleimidohexane (Pierce, Rockford, Ill.) is used to cross-link pIL-1β to the modified gpV (Partis et al. (1983) *J. Prot. Chem.* 2:263–277).

C. Assembly of Chemically Modified Bacteriophage λ

Packaging extracts from *E. coli* infected with bacteriophage λCI857 TrpE+Vam, prepared as described above, were mixed with gpV/pIL-1β as described by Rosenberg et al. (ibid). The resulting phage were purified by passing over an anti-IL-1β antibody column prepared as described for CNTF in Example 1.

D. Treatment of Starter Cell Population

The cDNA encoding IL-1β converting enzyme is cloned from the human acute monocytic-leukemia cell line, THP-1 as previously described (Cerretti et al. (1992) *Science* 256:97–100). The cDNA is cloned into the *E. coli* expression vector system pFLAG-1ff (International Biotechnologies, Inc., New Haven, Conn.). The transformed starter cell population is then chemically mutagenized according to Miller ((ed.) *Experiments in Molecular Genetics* (1972) Cold Spring Harbor, N.Y., pp. 121–139) with the goal of enhancing expression of the enzyme.

E. Screening the Treated Starter Cells for Production of Interleukin-1β Converting Enzyme The starter cells and feeder cells are the same as those described in Example 1. The chemically-modified bacteriophage are inactivated using antibodies as described in Example 1. A population of $10^8$ treated starter cells is plated with $10^8$ feeder cells and an experimentally determined number of inactivated, modified phage. The media is Minimal A (Miller (ed.) *Experiments in Molecular Genetics* (1972) Cold Spring Harbor, N.Y., p. 432) supplemented with glucose. Plates are incubated for 24 hours at 30° C. Colonies are grown in LB broth supplemented with ampicillin. Only treated starter cells will grow. A population of $10^2$ cells from this culture are mixed with $10^8$ feeder cells, and an experimentally determined number of inactivated, modified phage and the screening is repeated. Colonies are streaked onto LB agar plates supplemented with ampicillin. Resulting colonies produce interleukin-1β converting enzyme.

EXAMPLE 3

Screening for Genetically Engineered Yeast Producing Erythropoietin Using Chemically Modified Bacteriophage λ

Erythropoietin (EPO) (Sigma Chemical Company, St. Louis, Mo.) is chemically cross-linked to the cysteine residue of the modified gpV, as described in Example 2. An in vitro lambdoid packaging extract is made form *E. coli* carrying λCI857 TrpE+Vam, as described in Example 2. The EPO-gpV protein construct is added to the packaging extract followed by the addition of gpV. The resulting in vitro assembled phage containing EPO are purified by running the reaction mixture over an anti-EPO antibody column, as described in Example 1. Antibodies are prepared as described in Example 1. The EPO-modified phage are immobilized by cross-linking them to agarose (Wilchek et al. (1984) *Meth. Enzymol* 104:3). A mouse kidney cDNA library present in the yeast vector pYEUra3 is cloned into a proline excreting *S. cerevisiae* (ATCC Accession No. 20169, American Type Culture Collection, (Rockville, Md.) containing a deletion in a portion of the THR4 gene. The cloned library is prepared according to the method of Sambrook et al. ((eds.) *Molecular Cloning: A Laboratory Manual*, Cold Spring Harbor, N.Y., pp. 8.2–9.62 (1989)) or is commercially available (e.g., Clontech Laboratories, Palo Alto, Calif.). The feeder strain is the same as described in Examples 1 and 2.

Approximately $10^7$ treated starter cells are mixed with $10^8$ feeder cells and the experimentally determined amount of immobilized phage. The mixture is plated on minimal media lacking proline, threonine and tryptophan (0.67% yeast nitrogen base without amino acids (Difco Laboratories, Detroit, Mich.), 2% dextrose, 1.5% agar, pH 6.3). Plates are incubated for 48 hours at 30° C. Colonies are grown in minimal media plus threonine. Only treated starter cells will grow. A population of $10^2$ cells from this culture are mixed with $10^8$ feeder cells and the same amount of inactivated, modified phage and the screening is repeated. Colonies are streaked onto minimal agar plus threonine. Resulting colonies produce EPO.

EXAMPLE 4

Screening Treated Bacteria for Production of Staphylococcal Nuclease Using Chemically Modified Bacteriophage λ

A. Construction of Starter Cell

A strain of *C. glutamicum* that produces L-proline (ATCC Accession No. 21157) was obtained from the American Type Culture Collection (Rockville, Md.) (see U.S. Pat. No. 3,650,899). This strain was mutagenized with N-methyl-N'-nitro-nitrosoguanidine as described by Miller ((ed.) *Experiments in Molecular Genetics* (1972) Cold Spring Harbor, N.Y., pp. 125–129) to obtain a strain that requires L-threonine for growth.

B. Treatment of Starter Cell Population

A *Staphylococcus aureus* genomic DNA library is prepared from *S. aureus* strain ATCC Accession No. 27735 (American Type Culture Collection, Rockville, Md.) as described in *Molecular Cloning: A Laboratory Manual* (Sambrook et al., eds. (1989) Cold Spring Harbor, N.Y. pp.8.2–9.62. The vector used is pWST1 (Liebl et al. (1992) *J. Bacteriol.* 174:1854–1861). The resulting library was transformed into the starter cell population.

C. Assembly of Modified Bacteriophage λ

Bacteriophage λ is assembled from mixing packaging extracts made from λCI857 TrpE+Vam and modified gpV purified from pSYM1. All aspects of the assembly are described in previous examples.

D. Immobilization of Modified Bacteriophage λ

The phage are chemically cross-linked to a single-stranded DNA bound to a matrix. When DNA oligonucleotides are chemically synthesized, they are covalently attached to a matrix. Such matrix-bound DNA can be covalently cross-linked to the phage. Synthetic DNA oligionucleotides are made such that the terminal nucleotide contains a 5' amino linker. Such oligionucleotides are commercially obtainable from Integrated DNA Technologies, Inc. (Coralville, Iowa). The amino group is cross-linked to the terminal cysteine residue present in the modified gpV incorporated into the phage. The bifunctional cross-linking reagent, Sulfo-MBS (Pierce, Rockford, Ill.), is used according to the manufacturer's instructions.

E. Screening for Production of Staphylococcal Nuclease from Treated Starter Cells The feeder cells are the same as described in Example 1. A population of $10^8$ treated starter cells is plated with $10^8$ feeder cells and an experimentally determined number of inactivated, modified phage. The media is minial MM (Katsumata et al. (1984) *J. Bacteriol.* 159:306–311) supplemented with glucose. Plates are incubated for 24 hours at 30° C. Colonies are grown in minimal MM broth supplemented with threonine. Only treated starter cells will grow. $10^2$ cells from this culture are mixed with $10^8$ feeder cells and an experimentally determined number of inactivated, modified phage, and the screening is repeated. Colonies are streaked onto minimal MM agar plates supplemented with threonine. Resulting colonies produce Staphylococcal nuclease.

EXAMPLE 5

Isolation of a Transformed Human B-cell Producing Antibodies to Hepatitis C Virus A. Starter Cell Human B cells are isolated from the peripheral blood of a patient with chronic hepatitis who tests serpositive for HCV antigens (Berger (1979) *Meth. Enzymol.* 58:486–494). The B cell population is transformed with Epstein-Barr virus (Kim et al. (1993) *J. Virology* 67:7634) and transformants are selected for the ability to grow on softer-agar (Bouck et al. (1979) *Meth. Enzymol.* 58:296–302). Selected cells are then transformed with the pCAT-Control vector (Promega Corp., Madison, Wis.). This vector encodes ampicillin resistance permitting the selection of transformants on media containing ampicillin. No treatment of the starter cells is required because the cells were, in essence, pre-treated by exposure to HCV in the blood from which they were isolated.

B. Feeder Cell

*E. coli* strain P48 overproduces biotin (Pai (1972) *J. Bacteriol.* 112:1280–1287). The strain is mutagenized with N-methyl-N'-nitro-N-nitrosoguanidine and an auxotroph requiring products from the B cells for growth is selected by several rounds of first growing the cells in conditioned media followed by incubation in unconditioned media containing penicillin. By conditioned media is meant, media in which B cells have been grown and removed; the media thus contains excreted products of the cell line.

C. Construction of gpV/HCV Core Protein Fusion

The HCV core protein C22 has been cloned into *E. coli* and purified (Osborne et al. (1993) *FEBS Lett.* 324:2535–257). The protein is chemically cross-linked linked to the cysteine residue of the modified gpV encoded by pSYM1 as described in Example 2. The construction of pSYM1 and the method for purifying the modified gpV are set forth in the preferred embodiment.

D. Construction and Immobilization of Chemically Modified Bacteriophage λ

Chemically modified bacteriophage are assembled as described in Example 2 and are immobilized as described in Example 1 using anti-C22 antibodies prepared as described in Example 1.

E. Media

B cells are grown in Supplemented Dulbecco's modified Eagle's medium (Schneider (1989) *J. Immunol. Methods* 116:65–77). *E. coli* is grown in LB media. The media for screening is made by mixing 1 part of 2x concentrated Supplemented Dulbecco's modified Eagle's medium which has been passed over a streptavidin-agarose column (Pierce, Rockland, Ill.) to remove biotin with 1 part 0.6% agarose in water. The media is kept at 45° C. until ready for use.

F. Screening

Approximately $10^8$ feeder cells are mixed with an experimentally determined number of immobilized modified bacteriophage in 4 ml of media and plated in a petri dish. Then $10^5$ starter cells are mixed with another 4 ml of media and plated on top of the feeder cell layer. The plates are incubated for 7 days at 37° C. in an atmosphere of 5% $CO_2$, 95% air. Animal colonies are picked and plated for singles on the same media plus ampicillin. Resulting colonies should consist entirely of transformed B cells producing the desired antibody.

EXAMPLE 6

Isolation of a Plant Cell Producing Quinine

A. Starter Cell

A culture of *Digitalis ianata* (*D. ianata*) is established as described by Reynolds et al. (*Methods Enzymol.* (1979) 58:478–486). The culture is mutagenized with ethyl methanesulfonate as described by Thompson (*Meth. Enzymol. l* (1979) 58:308–322), and mutants requiring proline for growth are isolated.

B. Treatment of Starter Cells

The culture of starter cells is mutangenized with ethyl methanesulfonate as described above with the goal of enhancing the production of digoxin.

C. Feeder Cell

*E. coli* strain CR41, described in Example 1, overproduces proline. The strain is mutagenized with N-methyl-N'-nitro-N-nitrosoguanidine and an auxotroph requiring products from *D. ianata* for growth is selected by several rounds of first growing the cells in conditioned media followed by incubation in unconditioned media containing penicillin. By conditioned media is meant, media in which *D. ianata* has been grown and removed; the media thus contains excreted products of the cell line.

D. Construction of gpV/Digoxigenen Fusion

Digoxigenen-3-0-succinyl-[2-(N-maleimido)]-ethylamide (Boehringer Mannheim, Indianapolis, Ind.) is chemically cross-linked to the cysteine residue of the modified gpV encoded by pSYM1. The construction of pSYM1 and the method for purifying the modified gpV are set forth in the preferred embodiment.

E. Construction and Immobilization of Chemically Modified Bacteriophage λ

Chemically modified bacteriophage are assembled as described in EXAMPLE 2 and are immobilized as described in EXAMPLE 1 using anti-digoxin antibodies (Sigma Chemical Company, St. Louis, Mo.).

F. Media

*D. ianata* is grown in the media of Murashige et al. (*Physiol. Plant.* (1962) 15:473). *E. coli* is grown in LB media. The media for screening is the Murashige et al. media containing 0.6% Phytagar (Grand Island Biological Co., Grand Island, N.Y.).

G. Screening

Approximately $10^8$ feeder cells are mixed with an experimentally determined number of immobilized modified bacteriophage and plated in 4 ml of media. $10^5$ treated starter cells are mixed with 4 ml of media and plated on top of the layer containing the feeder cells and bacteriophage. The plates are incubated for 7 days at 27° C. Colonies arising in the top layer are picked and the individual cells are cloned as described above. Individual clones are screened again to verify the production of digoxin.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method for isolating a mutant cell that produces a desired compound, comprising:

(a) providing a starter cell selected from the group consisting of protista, monera, fungi, plant, animal and human cells which:

(i) is an auxotroph that has a requirement for a first molecule for its growth in a solid growth medium, and mutates spontaneously to lack the requirement at a frequency of less than $10^{-10}$ per cell division, the first molecule being selected from the group consisting of sugars, amino acids, growth factors, enzymes, cofactors, cytokines, lymphokines, trophic factors, fatty acids, lipids, interleukins, vitamins, and carbohydrates, the first molecule being other than the desired compound;

(ii) is resistant to lambdoid bacteriophage infection;

(iii) excretes a second molecule selected from the group consisting of a vitamin, amino acid, nucleic acid, cofactor, and sugar into the solid growth medium; and (iv) grows on a solid medium that supports the growth of bacteria;

(b) modifying the cellular DNA of the starter cell so as to increase the probability that the starter cell will excrete the desired compound;

(c) providing an *Escherichia coli* cell which:

(i) is an auxotroph that requires said second molecule and a polypeptide nutrient for growth on the solid growth medium, said second molecule being other than said first molecule or said nutrient, and said nutrient being other than said first molecule;

(ii) is susceptible to lambdoid bacteriophage infection; and (iii) excretes the first molecule into the solid growth medium;

(d) culturing a plurality of modified starter cells and *E. coli* cells together in the solid growth medium in the presence of a reversibly noninfective modified lambdoid bacteriophage having a head and a tail which:

(i) has reduced or no capacity for lytic infection;

(ii) carries a gene encoding said polypeptide nutrient; and (iii) further comprises a gpV protein having the amino acid sequence set forth in SEQ ID NO: 1 linked to an antibody or matrix through a target molecule, wherein the connection between the gpV protein and the target molecule is selected from the group consisting of truncation of the carboxy-terminal 24 amino acids of said sequence and genetic fusion of the truncated gpV protein to the target molecule, and substitution of an amino acid residue selected from the group consisting of histidine, cysteine, tryptophan, and tyrosine for amino acid position 246 of said sequence and chemical coupling of the target molecule to the substituted gpV protein, and wherein the linkage of the target molecule to the antibody or matrix has rendered the bacteriophage reversibly noninfective, the bacteriophage becoming infective if one of the modified starter cells excretes the desired compound, whereby the infective bacteriophage infects at least one of the *E. coli* cells, thereby enabling the infected *E. coli* cell to produce the nutrient;

(e) detecting a colony formed when the modified starter cell which excretes the desired compound excretes the first molecule and the infected *E. coli* cell excretes the second molecule, thereby enabling the *E. coli* and starter cells to grow; and (f) isolating the modified starter cell from the *E. coli* cells in the colony.

2. The method of claim 1 wherein the starter cell has a selectable phenotype which allows its isolation from the *E. coli* cell.

3. The method of claim 1 wherein the *E. coli* cell has a selectable phenotype which allows its isolation from the starter cell.

4. The method of claim 1 wherein the *E. coli* cells have been genetically engineered or mutagenized to become auxotropic.

5. The method of claim 1 wherein the starter cell and the *E. coli* cell belong to different genera.

6. The method of claim 1 wherein said starter cell and the *E. coli* cell are cells belonging to different species.

7. The method of claim 1 wherein the starter cell contains a mutation which renders it resistant to lambdoid bacteriophage infection.

8. The method of claim 7 wherein the mutation is in the bacteriophage receptor.

9. The method of claim 1 wherein the lambdoid bacteriophage expresses the CI lambda repressor, rendering it less capable of lytic infection.

10. The method of claim 1 wherein the starter cell and the *E. coli* cell are the same species.

11. The method of claim 1 wherein the desired compound is selected from the group consisting of polypeptides, peptides, hormones, nucleic acids, carbohydrates, lipids, glycoproteins, glycolipids, proteolipids, lipoproteins, lipopolysaccharides, vitamins, toxins, terpenes, antibiotics, and cofactors.

12. The method of claim 11 wherein the desired compound comprises a polypeptide selected from the group consisting of an enzyme, enzyme substrate, immunoglobulin, receptor, ligand, growth factor, toxin, cytokine, and hormone.

13. The method of claim 12 wherein the desired compound is an enzyme which cleaves the target molecule, thereby releasing the bacteriophage from the binding molecule.

14. The method of claim 1 wherein the desired compound is an unbound target molecule or a portion, analog, agonist, or antagonist thereof to which the binding molecule will bind.

15. The method of claim 1 wherein step (b) comprises mutagenizing the starter cell with a chemical mutagen.

16. The method of claim 1 wherein step (b) comprises genetically engineering the starter cell to express a mutator gene.

17. The method of claim 16 wherein the genetically engineered starter cell has a rate of mutation of at least $10^{-6}$ per nucleotide base per cell division.

18. The method of claim 1 wherein step (b) comprises transfecting or transforming the starter cell with a vector containing a gene encoding, or involved in the production of, the desired compound.

19. The method of claim 1 wherein the modification of the gpV protein is truncation of the carboxy-terminal 24 amino acids and genetic fusion of the truncated gpV protein to the target molecule.

20. The method of claim 1 wherein the modification of the gpV protein is substitution of an amino acid residue selected from the group consisting of histidine, cysteine, trytophan, and tyrosine for amino acid position 246 of said sequence and chemical coupling of the target molecule to the substituted gpV protein.

21. The method of claim 20 wherein the target molecule is selected from the group consisting of polypeptides, peptides, hormones, nucleic acids, carbohydrates, lipids, glycoproteins, glycolipids, proteolipids, lipoproteins, lipopolysaccharides, vitamins, toxins, terpenes, antibiotics, and cofactors.

22. The method of claim 20 wherein the gpV protein is covalently cross-linked to the target molecule.

* * * * *